US011435283B2

(12) United States Patent
Koohi et al.

(10) Patent No.: US 11,435,283 B2
(45) Date of Patent: Sep. 6, 2022

(54) OPTICALLY DETECTING MUTATIONS IN A SEQUENCE OF DNA

(71) Applicants: Somayyeh Koohi, Tehran (IR); Zahra Kavehvash, Tehran (IR); Ehsan Maleki, Kermanshah (IR); Hossein Babashah, Tehran (IR)

(72) Inventors: Somayyeh Koohi, Tehran (IR); Zahra Kavehvash, Tehran (IR); Ehsan Maleki, Kermanshah (IR); Hossein Babashah, Tehran (IR)

(73) Assignee: SHARIF UNIVERSITY OF TECHNOLOGY, Tehran (IR)

( * ) Notice: Subject to any disclaimer, the term of this patent is extended or adjusted under 35 U.S.C. 154(b) by 813 days.

(21) Appl. No.: 16/385,548

(22) Filed: Apr. 16, 2019

(65) Prior Publication Data

US 2020/0003677 A1 Jan. 2, 2020

Related U.S. Application Data

(60) Provisional application No. 62/658,612, filed on Apr. 17, 2018.

(51) Int. Cl.
*C12Q 1/68* (2018.01)
*G01N 21/00* (2006.01)
(Continued)

(52) U.S. Cl.
CPC ....... *G01N 21/1717* (2013.01); *C12Q 1/6869* (2013.01); *G01N 21/21* (2013.01);
(Continued)

(58) Field of Classification Search
CPC .. C12Q 1/6869; G01N 21/1717; G01N 21/21; G01N 21/6458; G01N 2021/1725;
(Continued)

(56) References Cited

U.S. PATENT DOCUMENTS 6,303,303 B1 10/2001 Green et al.
7,917,302 B2 3/2011 Rognes
(Continued)

OTHER PUBLICATIONS

Zhang et al. "DV-Curve: a novel intuitive tool for visualizing and analyzing DNA sequences." Bioinformatics 25, No. 9 (2009): 1112-1117.

(Continued)

*Primary Examiner* — Mark R Gaworecki
(74) *Attorney, Agent, or Firm* — Bajwa IP Law Firm; Haris Zaheer Bajwa

(57) ABSTRACT

A method for optically detecting mutations in a sequence of DNA is disclosed. The method includes generating an optically coded input sequence by optically coding an input sequence, generating an optically coded reference sequence by optically coding a reference sequence, generating an aligned sequence by overlapping the optically coded input sequence with the optically coded reference sequence, and determining a mutation in the input sequence with respect to the reference sequence. The input sequence includes an input arrangement of a plurality of elements. Each of the plurality of elements includes an element value of a plurality of element values. The reference sequence includes a reference arrangement of the plurality of elements. Each element of the aligned sequence includes one of a low-value element or a high-value element. The mutation is determined responsive to detecting the low-value element in the aligned sequence.

20 Claims, 19 Drawing Sheets

Specification includes a Sequence Listing.

(51) Int. Cl.
   *G02F 1/01*      (2006.01)
   *G16B 40/10*     (2019.01)
   *G16B 20/20*     (2019.01)
   *G01N 21/17*     (2006.01)
   *C12Q 1/6869*    (2018.01)
   *G01N 21/21*     (2006.01)
   *G16B 30/10*     (2019.01)

(52) U.S. Cl.
   CPC .......... *G02F 1/0102* (2013.01); *G02F 1/0126* (2013.01); *G16B 20/20* (2019.02); *G16B 40/10* (2019.02); *G01N 2021/1725* (2013.01); *G01N 2021/1765* (2013.01); *G16B 30/10* (2019.02)

(58) Field of Classification Search
   CPC .......... G01N 2021/1765; G02F 1/0102; G02F 1/0126; G16N 20/20; G16N 30/10; G16N 40/10
   See application file for complete search history.

(56)                References Cited

U.S. PATENT DOCUMENTS 3,239,140   A1   8/2012   Brodzik
   8,774,494   B2   7/2014   Staker
   2017/0199960 A1  7/2017   Ghose et al.

OTHER PUBLICATIONS

Mozafari et al. "DNA Sequence Alignment by Window based Optical Correlator." arXiv preprint arXiv:1710.01262 (2017).

Wavelength: 458 nm ← Wavelength: 632 nm ← → Wavelength: 634 nm

T C [A] G T A T [G][G][G][G] G A T

Wavelength: 614 nm ↵ ↳ Wavelength: 630 nm

FIG. 13

SEQUENCE LISTING

<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Synthetic Sequence

```
<400> SEQUENCE: 1
actgagcgac agatac                                               16

<210> SEQ ID NO 2
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 2
actgtgcgat cagtac                                               16

<210> SEQ ID NO 3
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 3
acgctcgaat cgatgc                                               16

<210> SEQ ID NO 4
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 4
acgctcgcat cgatgc                                               16

<210> SEQ ID NO 5
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 5
tcagtatggg ggat                                                 14

<210> SEQ ID NO 6
<211> LENGTH: 150
<212> TYPE: DNA
<213> ORGANISM: Artificial Sequence
<220> FEATURE:
<223> OTHER INFORMATION: Synthetic Sequence

<400> SEQUENCE: 6
agtttggctc ctgtcagcct ccataaaatc tgggacccaa gagccccact gagaggtaca      60
ggctggccct gtctcgtaat gcagctcggt tagcacaggg gctgatgtga caggctgtag     120
gttccgtaac ctcctgccat ctcaagcatg                                     150

<210> SEQ ID NO 7
<211> LENGTH: 150
<212> TYPE: DNA
<213> ORGANISM: Artificial Sequence
<220> FEATURE:
<223> OTHER INFORMATION: Synthetic Sequence

<400> SEQUENCE: 7
agtttggctc ctggcagcct ccataaaatc tgggacccga gccccactga gaggtacagg      60
```

```
ctggaccctg tctcgtaatg cagctcggtt agcacagggg caatgatgtg acaggctgtg        120
gttccgtaac ctcctgtatt ctcaagcatg                                         150
```

OPTICALLY DETECTING MUTATIONS IN A SEQUENCE OF DNA

CROSS-REFERENCE TO RELATED APPLICATION

This application claims the benefit of priority from U.S. Provisional Patent Application Ser. No. 62/658,612, filed on Apr. 17, 2018, and entitled "ALL-OPTICAL DNA SEQUENCE ALIGNMENT SYSTEM UTILIZING WAVELENGTH AND POLARIZATION MODULATION," which is incorporated herein by reference in its entirety.

TECHNICAL FIELD

The present disclosure generally relates to optical processing, and particularly, to optical bioinformatics and biophotonics.

BACKGROUND

Bioinformatics is an interdisciplinary field that expands methods and tools for biological data comprehension, and benefits from several sciences, such as computer science, statistics, mathematics, and engineering to expound and analyze biological data. As an important operation in bioinformatics, sequence alignment arranges sequences of DNA to identify regions of similarity and differences between sequences to detect probable genetic diseases. Each DNA sequence may be represented with a string of A/G/T/C characters; each is called a nucleotide, and composed of either of adenine (A), guanine (G), thymine (T), or cytosine (C).

A purpose of sequence alignment may be locating permanent changes in a nucleotide sequence, generally denoted as mutations. Mutations may be classified either as small-scale mutations or as large-scale mutations. A small scale mutation which may affect a small gene in one or a few nucleotides may cause a nucleotide base substitution, insertion, or deletion of a genetic material, DNA, or RNA. The mutations, which may happen randomly, may cause genetic disorders. Therefore, detecting and locating point mutations may be useful for detecting genetic diseases.

As a powerful two-dimensional (2D) graphical method, DV-curve (dual-vector curve) coding method, by avoiding degeneracy and loss of information, may offer good visualization to represent long sequences in 2D space. Therefore, DV-curve coding may be a useful tool for detecting and locating mutations in DNA sequences. However, a low speed and an incomprehensible output of DV-curve coding may limit its application.

There is, therefore, a need for a high-speed method for utilizing DV-curve coding for detecting mutations in a sequence. There is also a need for a system for a high-speed implementation of the DV-curve method for mutation detection in a sequence.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for optically detecting mutations in a sequence of DNA. An exemplary method may include generating an optically coded input sequence by optically coding an input sequence, generating an optically coded reference sequence by optically coding a reference sequence, generating an aligned sequence by correlating the optically coded input sequence with the optically coded reference sequence, and determining a mutation in the input sequence with respect to the reference sequence. In an exemplary embodiment, the input sequence may include an input arrangement of a plurality of elements. Each of the plurality of elements may include an element value of a plurality of element values. In an exemplary embodiment, the reference sequence may include a reference arrangement of the plurality of elements. In an exemplary embodiment, each element of the aligned sequence may include one of a low-value element or a high-value element. In an exemplary embodiment, the mutation may be determined responsive to detecting the low-value element in the aligned sequence.

In an exemplary embodiment, optically coding the input sequence may include assigning a bright-pixels pattern of a plurality of bright-pixels patterns to each of the plurality of elements, generating a primary coded input sequence by arranging the plurality of bright-pixels patterns according to the input arrangement, and assigning a wavelength to an element of the primary coded input sequence based on neighboring elements of a corresponding element in the input sequence. In an exemplary embodiment, the bright-pixels pattern may include a sequence of bright pixels.

In an exemplary embodiment, assigning the bright-pixels pattern to each of the plurality of elements may include assigning a respective pair of successive bright pixels to each of the plurality of elements. In an exemplary embodiment, the respective pair of successive bright pixels may be associated with a dual-vector (DV)-curve representation of a respective element value of the plurality of element values.

In an exemplary embodiment, optically coding the reference sequence may include generating a primary coded reference sequence by arranging the plurality of bright-pixels patterns according to the reference arrangement, and assigning the wavelength to an element of the primary coded reference sequence based on neighboring elements of a corresponding element in the reference sequence.

In an exemplary embodiment, generating the aligned sequence may include generating a plurality of vertically repeated reference sequences from the optically coded reference sequence, generating a plurality of horizontally repeated reference sequences from the plurality of vertically repeated reference sequences, generating a first two-dimensional image by overlapping the optically coded input sequence with each of the optically coded reference sequence, the plurality of vertically repeated reference sequences, and the plurality of horizontally repeated reference sequences, generating a first optically thresholded two-dimensional image from the first two-dimensional image, generating a first one-dimensional image from the first optically thresholded two-dimensional image, and extracting a first sequence of pixels from the first one-dimensional image. Each of the plurality of vertically repeated reference sequences may include a repetition of the optically coded reference sequence shifted in a vertical direction by a first vertical shift, and each of the plurality of horizontally repeated reference sequences may include a repetition of one of the plurality of vertically repeated reference sequences shifted in a horizontal direction by a first horizontal shift. In an exemplary embodiment, the first two-dimensional image may include a first plurality of columns, and each of the first plurality of columns may include a first vertical arrangement of pixels. Each pixel of the first vertical arrangement of pixels may include one of a dark pixel or a bright pixel.

In an exemplary embodiment, generating the first optically thresholded two-dimensional image may include replacing the bright pixel with the dark pixel in the first vertical arrangement of pixels responsive to detecting that a brightness level of the bright pixel is lower than a brightness threshold. In an exemplary embodiment, generating the first one-dimensional image may include projecting a first column of the first plurality of columns into a first pixel of a first pixel array. In an exemplary embodiment, projecting the first column into the first pixel may include including the bright pixel in the first pixel responsive to determining that the first column includes the bright pixel. In an exemplary embodiment, extracting the first sequence of pixels may include mapping the first pixel to a first neighboring pixels subset of the first pixel array responsive to including the bright pixel in the first pixel.

In an exemplary embodiment, determining the mutation in the input sequence may include detecting a respective pair of successive dark pixels in the first sequence of pixels. The respective pair of successive dark pixels may be associated with the low-value element.

In an exemplary embodiment, generating the aligned sequence may further include generating a plurality of vertically repeated input sequences from the optically coded input sequence, generating a plurality of horizontally repeated input sequences from the plurality of vertically repeated reference sequences, generating a second two-dimensional image by overlapping the optically coded reference sequence with each of the optically coded input sequence, the plurality of vertically repeated input sequences, and the plurality of horizontally repeated input sequences, generating a second optically thresholded two-dimensional image from the second two-dimensional image, generating a second one-dimensional image from the second optically thresholded two-dimensional image, and extracting a second sequence of pixels from the second one-dimensional image. Each of the plurality of vertically repeated input sequences may include a repetition of the optically coded input sequence shifted in the vertical direction by a second vertical shift, and each of the plurality of horizontally repeated input sequences may include a repetition of one of the plurality of vertically repeated reference sequences shifted in the horizontal direction by a second horizontal shift. In an exemplary embodiment, the second two-dimensional image may include a second plurality of columns, and each of the second plurality of columns may include a second vertical arrangement of pixels. Each pixel of the second vertical arrangement of pixels may include one of the dark pixel or the bright pixel.

In an exemplary embodiment, generating the second optically thresholded two-dimensional image may include replacing the bright pixel with the dark pixel in the second vertical arrangement of pixels responsive to detecting that the brightness level of the bright pixel is lower than the brightness threshold. In an exemplary embodiment, generating the second one-dimensional image may include projecting a second column of the second plurality of columns into a second pixel of a second pixel array. In an exemplary embodiment, projecting the second column into the second pixel may include including the bright pixel in the second pixel responsive to determining that the second column includes the bright pixel. In an exemplary embodiment, extracting the second sequence of pixels may include mapping the second pixel to a second neighboring pixels subset of the second pixel array responsive to including the bright pixel in the second pixel.

In an exemplary embodiment, determining the mutation in the input sequence may include determining a substitution in the input sequence by detecting a first pair of successive dark pixels in the first sequence of pixels and detecting a second pair of successive dark pixels in the second sequence of pixels, determining an insertion in the input sequence by detecting a third pair of successive dark pixels in the first sequence of pixels and detecting a fourth pair of successive bright pixels in the second sequence of pixels, and determining a deletion in the input sequence by detecting a fifth pair of successive bright pixels in the first sequence of pixels and detecting a sixth pair of successive dark pixels in the second sequence of pixels. In an exemplary embodiment, the first pair may be associated with the second pair, and each of the first pair and the second pair may be associated with the low-value element. In an exemplary embodiment, the third pair may be associated with the fourth pair. The third pair may be associated with the low-value element and the fourth pair may be associated with the high-value element. In an exemplary embodiment, the fifth pair may be associated with the sixth pair. The fifth pair may be associated with the high-value element and the sixth pair may be associated with the low-value element.

In an exemplary embodiment, the present disclosure describes an exemplary system for optically detecting mutations in a sequence of DNA. An exemplary system may include a light source, a first optical filter, a second optical filter, and a detector. In an exemplary embodiment, the light source may be configured to illuminate an input optical signal. In an exemplary embodiment, the first optical filter may be configured to generate an optically coded input signal from the input optical signal based on an input sequence. The input sequence may include an input arrangement of a plurality of elements, and each of the plurality of elements may include an element value of a plurality of element values. In an exemplary embodiment, the second optical filter may be configured to generate an aligned signal by overlapping the optically coded input signal with a reference sequence. In an exemplary embodiment, the reference sequence may include a reference arrangement of the plurality of elements. In an exemplary embodiment, the detector may be configured to receive and display the aligned signal.

In an exemplary embodiment, the first optical filter may include a first polarizer and a first electrically tunable color filter. In an exemplary embodiment, the first polarizer may be configured to generate a polarized input signal from the input optical signal. In an exemplary embodiment, the first electrically tunable color filter may be configured to generate a primary coded input signal from the polarized input signal by overlapping the polarized input signal with a first arrangement of a plurality of bright-pixels patterns on the first electrically tunable color filter and generate the optically coded input signal from the primary coded input signal by modifying a wavelength of an element of the primary coded input signal based on neighboring elements of a corresponding element in the input sequence. In an exemplary embodiment, the first arrangement may correspond to the input arrangement. In an exemplary embodiment, each of the plurality of bright-pixels patterns may be assigned to each of the plurality of elements. Each of the plurality of bright-pixels patterns may include a sequence of bright pixels. In an exemplary embodiment, the sequence of bright pixels may include a respective pair of successive bright pixels that may be associated with DV-curve representation of a respective element value of the plurality of element values.

In an exemplary embodiment, the second optical filter may include a second polarizer, a second electrically tunable color filter, a first optical thresholder, a first cylindrical lens, a first diffraction grating, and a first mirror. In an exemplary embodiment, the second polarizer may be configured to generate a polarized coded input signal from the optically coded input signal. In an exemplary embodiment, the second electrically tunable color filter may be configured to generate a first primary image from the polarized coded input signal by overlapping the polarized coded input signal with each of a second arrangement of the plurality of bright-pixels patterns on the second electrically tunable color filter, a first plurality of vertical arrangements of the plurality of bright-pixels patterns on the second electrically tunable color filter, and a first plurality of horizontal arrangements of the plurality of bright-pixels patterns on the second electrically tunable color filter, and generate the first two-dimensional image from the first primary image by modifying a wavelength of each element of the first primary image based on neighboring elements of a corresponding element in the reference sequence. In an exemplary embodiment, the second arrangement may correspond to the reference arrangement. Each of the first plurality of vertical arrangements may include a repetition of the second arrangement shifted in the vertical direction of the second electrically tunable color filter by the first vertical shift, and each of the first plurality of horizontal arrangements may include a repetition of one of the first plurality of vertical arrangements shifted in the horizontal direction of the second electrically tunable color filter by the first horizontal shift.

In an exemplary embodiment, the first optical thresholder may be configured to generate the first optically thresholded two-dimensional image from the first two-dimensional image by blocking an illumination of the bright pixel responsive to detecting that the brightness level of the bright pixel is lower than the brightness threshold. In an exemplary embodiment, the first cylindrical lens may be configured to generate the first one-dimensional image from the first optically thresholded two-dimensional image by projecting the first column of the first plurality of columns into the first pixel of the first pixel array.

In an exemplary embodiment, the first diffraction grating may be configured to receive an illumination of the first one-dimensional image and generate a first segment of the aligned signal. In an exemplary embodiment, the illumination of the first one-dimensional image may include a first plurality of rays, and each of the first plurality of rays may be associated with the bright pixel. In an exemplary embodiment, the first diffraction grating may be configured to generate the first segment of the aligned signal by diffracting each of the first plurality of rays into a first plurality of diffracted rays. In an exemplary embodiment, the first plurality of diffracted rays may be associated with the first neighboring pixels subset of the first pixel array responsive to including the bright pixel in the first pixel. In an exemplary embodiment, the first mirror may be configured to reflect the first segment on the detector.

In an exemplary embodiment, the light source may include a laser, a beam splitter, a second diffraction grating, a first optical lens, a second mirror, a third diffraction grating, and a second optical lens. In an exemplary embodiment, the laser may be configured to emit a beam of light. In an exemplary embodiment, the beam splitter may be configured to split the beam into a first split beam and a second split beam. In an exemplary embodiment, the second diffraction grating may be configured to diffract the first split beam into a first plurality of diffracted beams. In an exemplary embodiment, the first optical lens may be configured to generate the input optical signal by producing a first plurality of parallel beams from the first plurality of diffracted beams. In an exemplary embodiment, the second mirror may be configured to produce a reflection of the second split beam. In an exemplary embodiment, the third diffraction grating may be configured to diffract the reflection of the second split beam into a second plurality of diffracted beams. In an exemplary embodiment, the second optical lens may be configured to generate a reference optical signal by producing a second plurality of parallel beams from the second plurality of diffracted beams.

In an exemplary embodiment, an exemplary system may further include a third optical filter and a fourth optical filter. In an exemplary embodiment, the third optical filter may include a third polarizer and a third electrically tunable color filter. In an exemplary embodiment, the third polarizer may be configured to generate a polarized reference signal from the reference optical signal. In an exemplary embodiment, the third electrically tunable color filter may be configured to generate a primary coded reference signal from the polarized reference signal by overlapping the polarized reference signal with a third arrangement of the plurality of bright-pixels patterns on the third electrically tunable color filter and generate an optically coded reference signal from the primary coded reference signal by modifying a wavelength of each element of the primary coded reference signal based on neighboring elements of a corresponding element in the reference sequence. In an exemplary embodiment, the third arrangement may correspond to the reference arrangement.

In an exemplary embodiment, the fourth optical filter may include a fourth polarizer and, fourth electrically tunable color filter, a second optical thresholder, a second cylindrical lens, a fourth diffraction grating, and a third mirror. In an exemplary embodiment, the fourth polarizer may be configured to generate a polarized coded reference signal from the optically coded reference signal based on the input arrangement. In an exemplary embodiment, the fourth electrically tunable color filter may be configured to generate a second primary image from the polarized coded reference signal by overlapping the polarized coded reference signal with each of a fourth arrangement of the plurality of bright-pixels patterns on the fourth electrically tunable color filter, a second plurality of vertical arrangements of the plurality of bright-pixels patterns on the fourth electrically tunable color filter, and a second plurality of horizontal arrangements of the plurality of bright-pixels patterns on the fourth electrically tunable color filter, and generate the second two-dimensional image from the second primary image by modifying a wavelength of an element of the second primary image based on neighboring elements of a corresponding element in the input sequence. In an exemplary embodiment, the fourth arrangement may correspond to the input arrangement. In an exemplary embodiment, each of the second plurality of vertical arrangements may include a repetition of the fourth arrangement shifted in the vertical direction of the fourth electrically tunable color filter by the second vertical shift, and each of the second plurality of horizontal arrangements may include a repetition of one of the second plurality of vertical arrangements shifted in the horizontal direction of the fourth electrically tunable color filter by the second horizontal shift.

In an exemplary embodiment, the second optical thresholder may be configured to generate the second optically thresholded two-dimensional image from the second two-dimensional image by blocking an illumination of the bright pixel responsive to detecting that the brightness level of the bright pixel is lower than the brightness threshold. In an exemplary embodiment, the second cylindrical lens may be configured to generate the second one-dimensional image from the second optically thresholded two-dimensional image by projecting the second column of the second plurality of columns into the second pixel of the second pixel array.

In an exemplary embodiment, the fourth diffraction grating may be configured to receive an illumination of the second one-dimensional image and generate a second segment of the aligned signal. In an exemplary embodiment, the illumination of the second one-dimensional image may include a second plurality of rays, and each of the second plurality of rays may be associated with the bright pixel. In an exemplary embodiment, the fourth diffraction grating may be configured to generate the second segment of the aligned signal by diffracting each of the second plurality of rays into a second plurality of diffracted rays. In an exemplary embodiment, the second plurality of diffracted rays may be associated with the second neighboring pixels subset of the second pixel array responsive to including the bright pixel in the second pixel. In an exemplary embodiment, the third mirror may be configured to reflect the second segment on the detector.

In an exemplary embodiment, each of the first electrically tunable color filter, the second electrically tunable color filter, the third electrically tunable color filter, and the fourth electrically tunable color filter may include a plurality of graphene-based spatial light modulators. A graphene-based spatial light modulator of the plurality of graphene-based spatial light modulators may be configured to prevent transmission of a light beam associated with a wavelength range responsive to a voltage applied to the graphene-based spatial light modulator. In an exemplary embodiment, the graphene-based spatial light modulator may include a conductive layer, a dielectric layer mounted on the conductive layer, and a graphene layer mounted on the dielectric layer. In an exemplary embodiment, the graphene layer may include a plurality of parallel graphene sheets.

In an exemplary embodiment, the conductive layer may include a gold nanostructure. In an exemplary embodiment, the dielectric layer may include a silicon dioxide material. In an exemplary embodiment, a space between each adjacent graphene sheets of the plurality of parallel graphene sheets may lie in a range of about 95 nm and about 105 nm. In an exemplary embodiment, a width of each of the plurality of parallel graphene sheets may lie in a range of about 195 nm and about 205 nm.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 13 shows a DNA sequence, consistent with one or more exemplary embodiments of the present disclosure.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for detecting mutations in DNA sequences, as well as variations including substitution, insertion, and deletion in a sequence of elements. An exemplary method may optically code each element of an input sequence (for example, a nucleotide in a DNA sequence) with a visual pattern (for example, a pattern of pixels) to produce a visual representation of the input sequence. The visual representation may then be repeated in vertical and horizontal directions to generate a two-dimensional image that includes several representations of the input sequence. This two-dimensional image may then be overlapped with a reference sequence (for example, by illuminating an optical representation of the reference sequence on the two-dimensional image) to detect mutations by detecting dark pixels in a resultant overlapped image.

The above process may be repeated by replacing the input and reference sequences. In an exemplary method, the repetition of the above process may be performed in parallel in order to simultaneously obtain two resultant images, thereby increasing the implementation speed. By comparing the two resultant images, the mutation type (i.e., substitution, insertion, or deletion) may be determined. An exemplary method may also be applied for local alignment of the input and reference sequences.

Figure 1A:
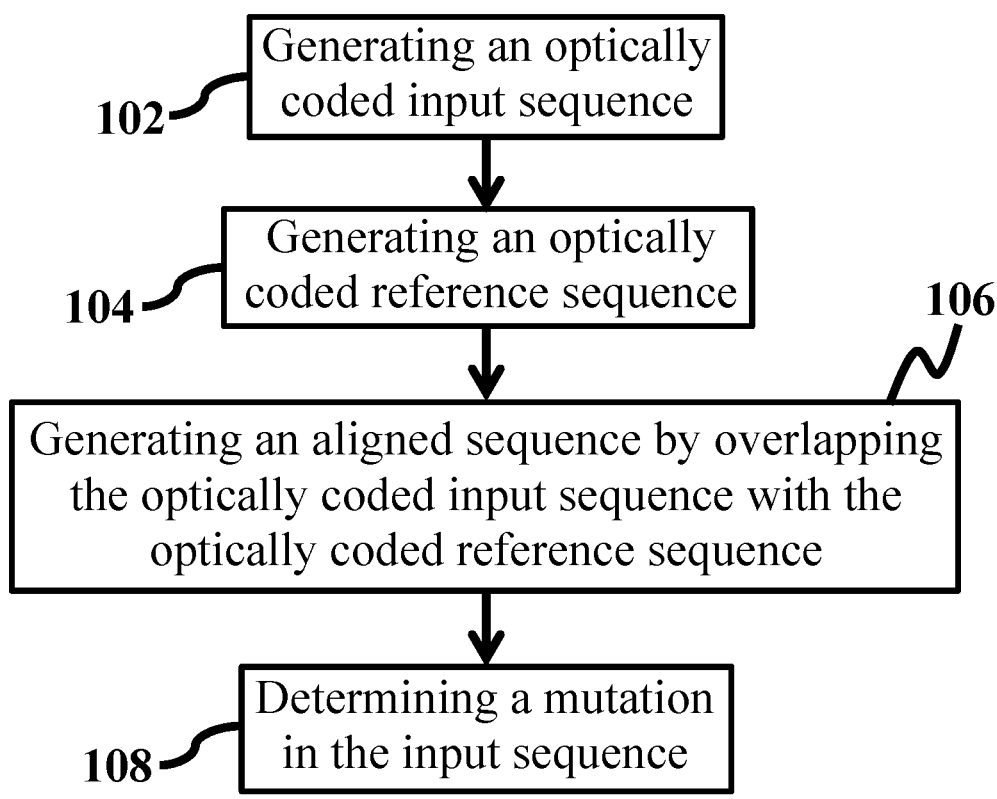
FIG. 1A shows a flowchart of a method for optically detecting mutations in a sequence of DNA, consistent with one or more exemplary embodiments of the present disclosure.

FIG. 1A shows a flowchart of a method for optically detecting mutations in a sequence of DNA, consistent with one or more exemplary embodiments of the present disclosure. An exemplary method 100 may include generating an optically coded input sequence by optically coding an input sequence (step 102), generating an optically coded reference sequence by optically coding a reference sequence (step 104), generating an aligned sequence by overlapping the optically coded input sequence with the optically coded reference sequence (step 106), and determining a mutation in the input sequence with respect to the reference sequence (step 108).

Figure 2:
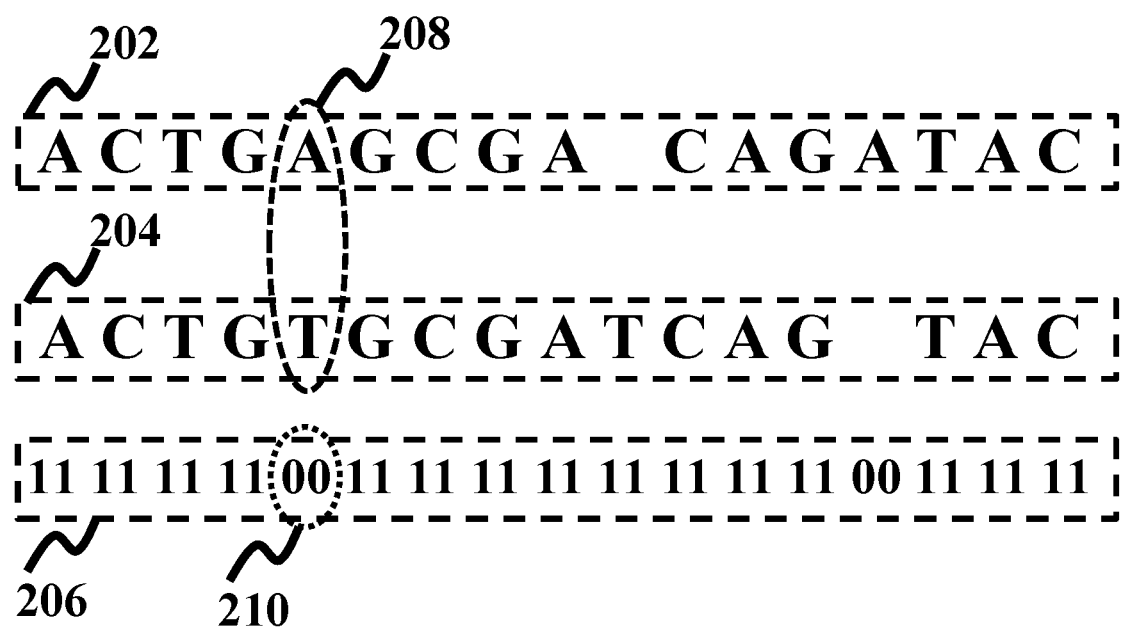
FIG. 2 shows an input sequence, a reference sequence, and an aligned sequence, consistent with one or more exemplary embodiments of the present disclosure.

For further detail with regards to method 100, FIG. 2 shows an input sequence, a reference sequence, and an aligned sequence, consistent with one or more exemplary embodiments of the present disclosure. An exemplary input sequence 202 (SEQ ID NO: 1) may include an input arrangement of a plurality of elements. In an exemplary embodiment, each of the plurality of elements may include a nucleotide of a DNA. Each of the plurality of elements may include an element value of a plurality of element values. In an exemplary embodiment, each element value may include one of adenine (represented by A in input sequence 202 (SEQ ID NO: 1)), guanine (represented by G in input sequence 202 (SEQ ID NO: 1)), thymine (represented by T in input sequence 202 (SEQ ID NO: 1)), and cytosine (represented by C in input sequence 202 (SEQ ID NO: 1)). An exemplary reference sequence 204 (SEQ ID NO: 2) may include a reference arrangement of the plurality of elements. Each element of an exemplary aligned sequence 206 may include one of a low-value element (represented by "00" in aligned sequence 206) and a high-value element (represented by "11" in aligned sequence 206). In an exemplary embodiment, determining a mutation 208 may include determining mutation 208 responsive to detecting presence of a low-value element 210 in aligned sequence 206.

Figure 1B:
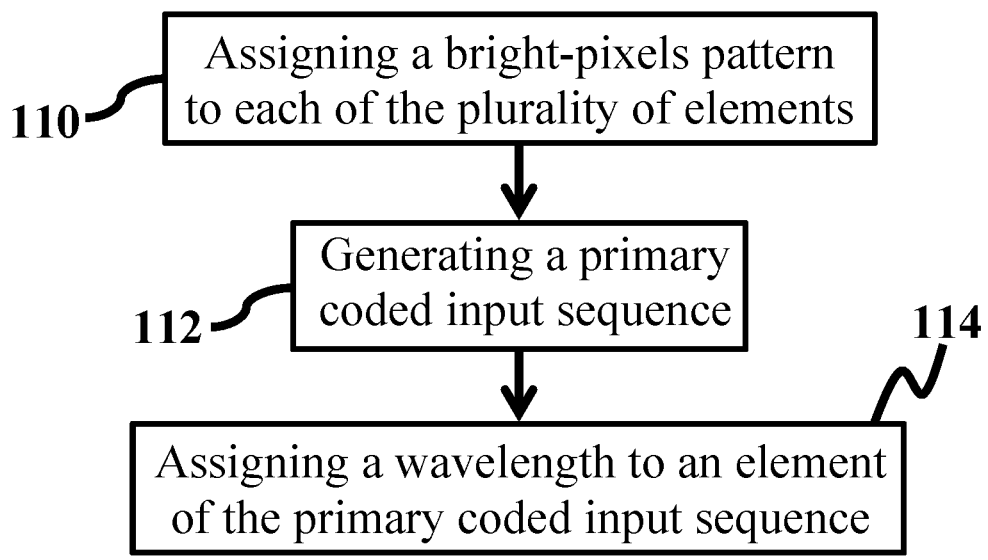
FIG. 1B shows a flowchart for optically coding an input sequence, consistent with one or more exemplary embodiments of the present disclosure.

In further detail with respect to step 102, FIG. 1B shows a flowchart for optically coding the input sequence, consistent with one or more exemplary embodiments of the present disclosure. In an exemplary embodiment, optically coding the input sequence in step 102 may include assigning a bright-pixels pattern of a plurality of bright-pixels patterns to each of the plurality of elements (step 110), generating a primary coded input sequence by arranging the plurality of bright-pixels patterns according to the input arrangement (step 112), and assigning a wavelength to an element of the primary coded input sequence based on neighboring elements of a corresponding element in the input sequence (step 114). In an exemplary embodiment, the bright-pixels pattern may include a sequence of bright pixels.

In an exemplary embodiment, assigning the bright-pixels pattern to each of the plurality of elements (step 110) may include assigning a respective pair of successive bright pixels to each of the plurality of elements. In an exemplary embodiment, the respective pair of successive bright pixels may be associated with a dual-vector (DV)-curve representation of a respective element value of the plurality of element values.

Figure 3:
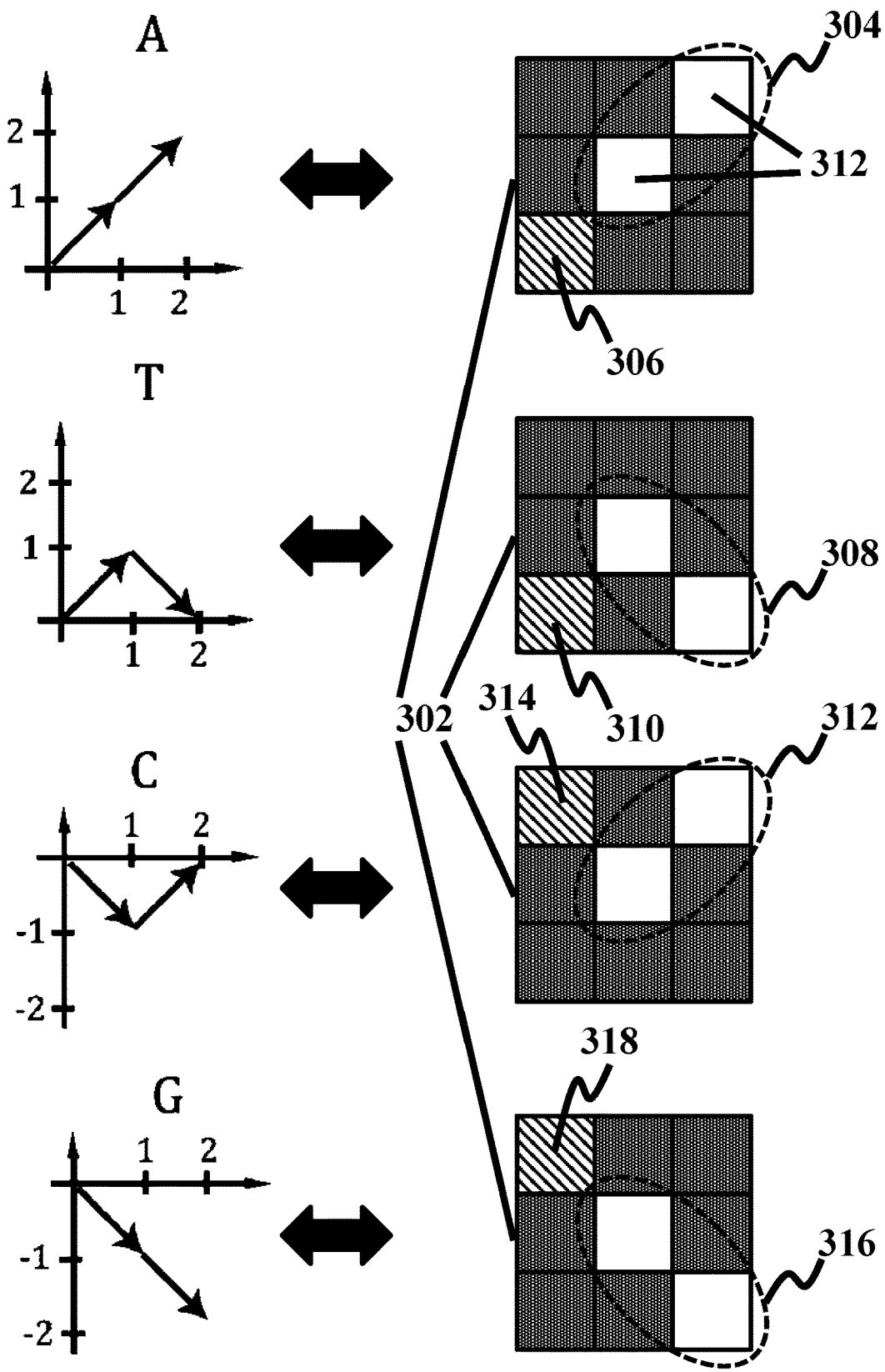
FIG. 3 shows a plurality of bright-pixels patterns, consistent with one or more exemplary embodiments of the present disclosure.

For further detail with regards to step 110, FIG. 3 shows a plurality of bright-pixels patterns 302, consistent with one or more exemplary embodiments of the present disclosure. In an exemplary embodiment, each of plurality of bright-pixels patterns 302 may include a sequence of bright pixels. For better understanding of the plurality of bright-pixels patterns 302, a position of a reference pixel is illustrated shown in FIG. 3. In an exemplary embodiment, each sequence of bright pixels may start after the reference pixel. For example, a sequence 304 may start after a reference pixel 306, a sequence 308 may start after a reference pixel 310, a sequence 312 may start after a reference pixel 314, and a sequence 316 may start after a reference pixel 318. In an exemplary embodiment, each sequence of bright pixels may include a respective pair of successive bright pixels. For example, sequence 304 may include a respective pair of successive bright pixels 312. In an exemplary embodiment, each pair of successive bright pixels and a respective sequence may be associated with a DV-curve representation of a respective element value of the plurality of element values. For example, sequence 304 may be associated with a DV-curve representation of adenine (represented by A in FIG. 3), sequence 308 may be associated with a DV-curve representation of thymine (represented by T in FIG. 3), sequence 312 may be associated with a DV-curve representation of cytosine (represented by C in FIG. 3), and sequence 316 may be associated with a DV-curve representation of guanine (represented by G in FIG. 3).

Figure 4:
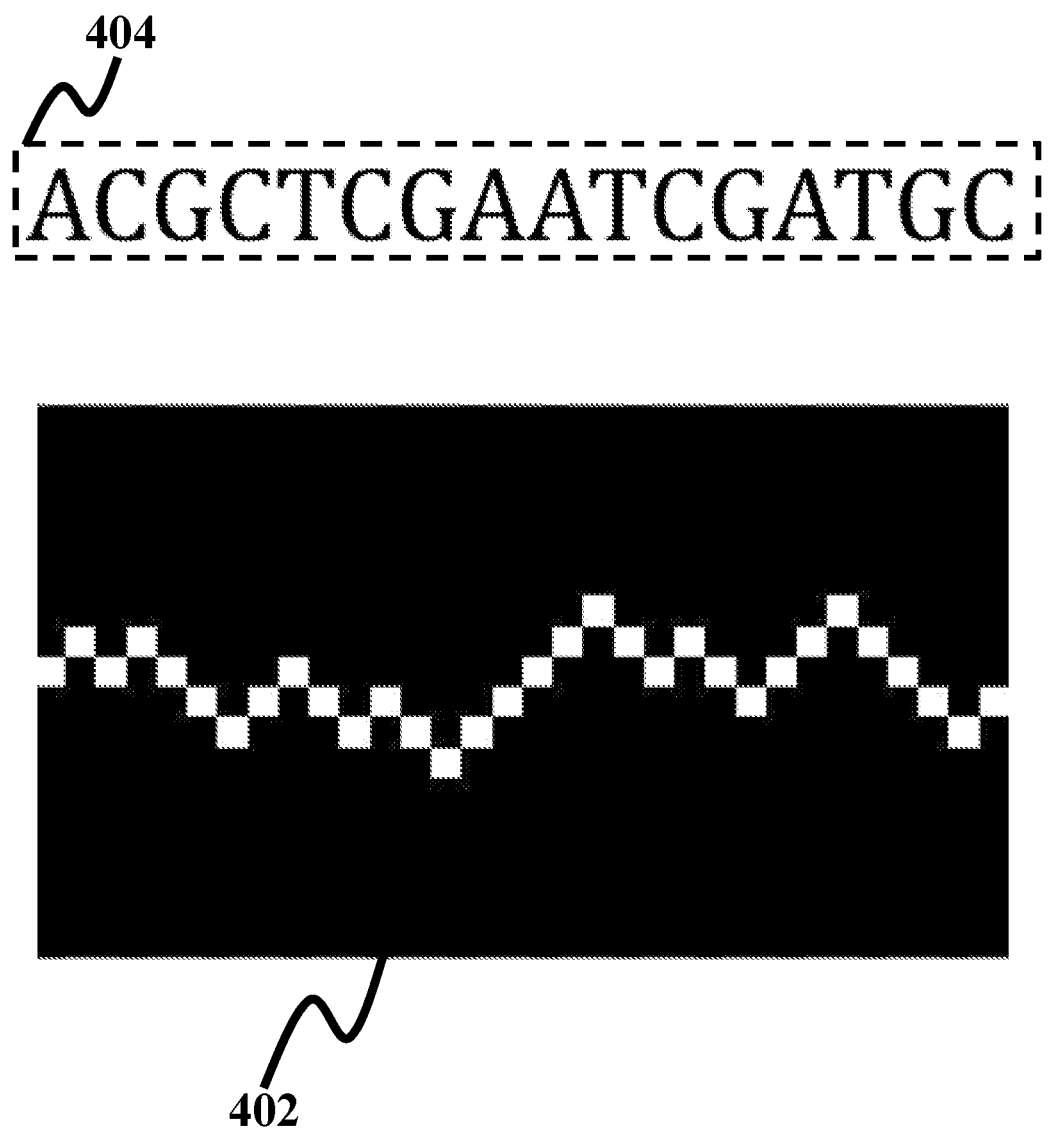
FIG. 4 shows an arrangement of a plurality of bright-pixels patterns, consistent with one or more exemplary embodiments of the present disclosure.

For further detail with respect to step 112, FIG. 4 shows an arrangement 402 of plurality of bright-pixels patterns 302, consistent with one or more exemplary embodiments of the present disclosure. In an exemplary embodiment, plurality of bright-pixels patterns 302 may be arranged in arrangement 402 according to an input arrangement 404 of an exemplary input sequence (SEQ ID NO: 3).

In an exemplary embodiment, assigning the wavelength to each of the elements of the primary coded input sequence (step 114) may include assigning a wavelength $W_{N_i}$ to an $N_i^{th}$ element value of the plurality of element values according to an operation defined by the following:

$$W_{N_i} = w_{N_i} - (4 \times S \times k_{N_i,N_i-1}) - S \times k_{N_i,N_i+1} + S(R-1),\qquad \text{Equation (1)}$$

where:

$w_{N_i}$ is a modulation wavelength assigned to the $N_i^{th}$ element value associated with an $i^{th}$ element of one of the input sequence or the reference sequence, S is a wavelength coding resolution, $k_{m,n}$ is a constant associated with an $m^{th}$ element value and an $n^{th}$ element value of the plurality of element values, and R is a number of successive repetitions of the $i^{th}$ element in one of the input sequence or the reference sequence.

In an exemplary embodiment, $w_{N_i}$ may be set to about 480 nm for element value adenine (A), about 530 nm for element value thymine (T), about 580 nm for element value cytosine (C), and about 630 nm for element value guanine (G). Table 1 shows values of $k_{m,n}$ for different combinations of m and n, corresponding to different combinations of element values.

TABLE 1

Values of $k_{m,n}$ for different combinations of m and n

| m | n | | | |
|---|---|---|---|---|
|   | A | T | C | G |
| A | 0 | 1 | 2 | 3 |
| T | 1 | 0 | 3 | 2 |
| C | 2 | 3 | 0 | 1 |
| G | 3 | 2 | 1 | 0 |

In an exemplary embodiment, R may be set to 1 for a first unrepeated presence of each element value at an $i^{th}$ position in the input sequence. If the element value is repeated in a position i'=i+1, the value of R may be increased by 1. Therefore, R may increase if the same element value is chained continuously in the input sequence, such as "AAAAAA". In an exemplary embodiment, a maximum value of R may be set to 10, i.e., more than 9 successive repetitions of an element value in the input sequence may not increase the value of R.

Referring again to FIG. 1A, in an exemplary embodiment, optically coding the reference sequence in step 104 may include generating a primary coded reference sequence by arranging the plurality of bright-pixels patterns according to the reference arrangement, which may be similar to arranging plurality of bright-pixels patterns 302 illustrated in FIGS. 3 and 4. In an exemplary embodiment, optically coding the reference sequence in step 104 may further include assigning the wavelength to an element of the primary coded reference sequence based on neighboring elements of a corresponding element in the reference sequence. In an exemplary embodiment, the wavelength assignment to each element of the primary coded reference sequence may be performed according to Equation (1), similar to the wavelength assignment to each element of the primary coded input sequence.

Figure 1C:
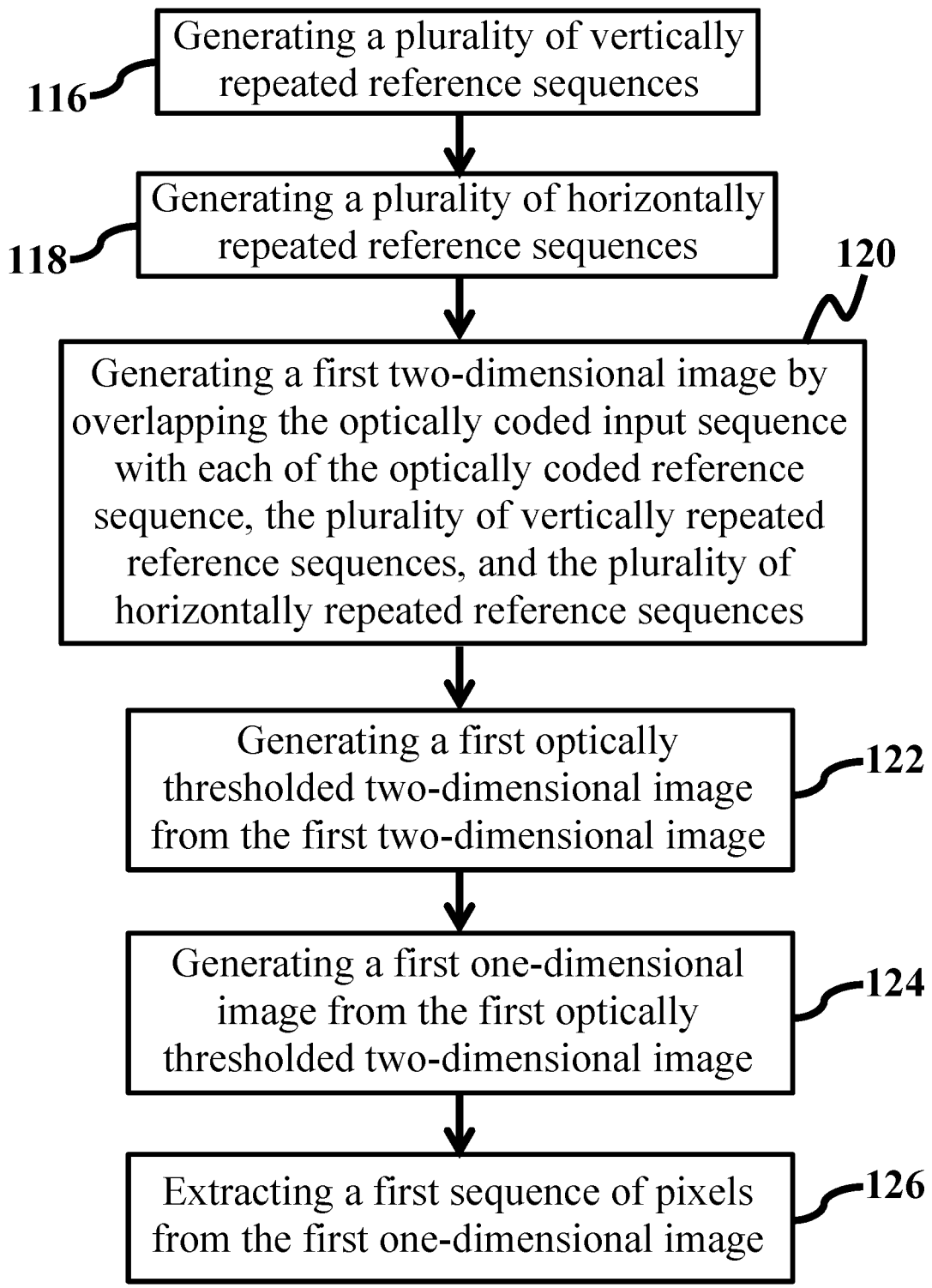
FIG. 1C shows a flowchart for generating an aligned sequence, consistent with one or more exemplary embodiments of the present disclosure.

In further detail with regards to step 106, FIG. 1C shows a flowchart for generating the aligned sequence, consistent with one or more exemplary embodiments of the present disclosure. In an exemplary embodiment, generating the aligned sequence (step 106) may include generating a plurality of vertically repeated reference sequences from the optically coded reference sequence (step 116), generating a plurality of horizontally repeated reference sequences from the plurality of vertically repeated reference sequences (step 118), generating a first two-dimensional image by overlapping the optically coded input sequence with each of the optically coded reference sequence, the plurality of vertically repeated reference sequences, and the plurality of horizontally repeated reference sequences (step 120), generating a first optically thresholded two-dimensional image from the first two-dimensional image (step 122), generating a first one-dimensional image from the first optically thresholded two-dimensional image (step 124), and extracting a first sequence of pixels from the first one-dimensional image (step 126).

Figure 5:
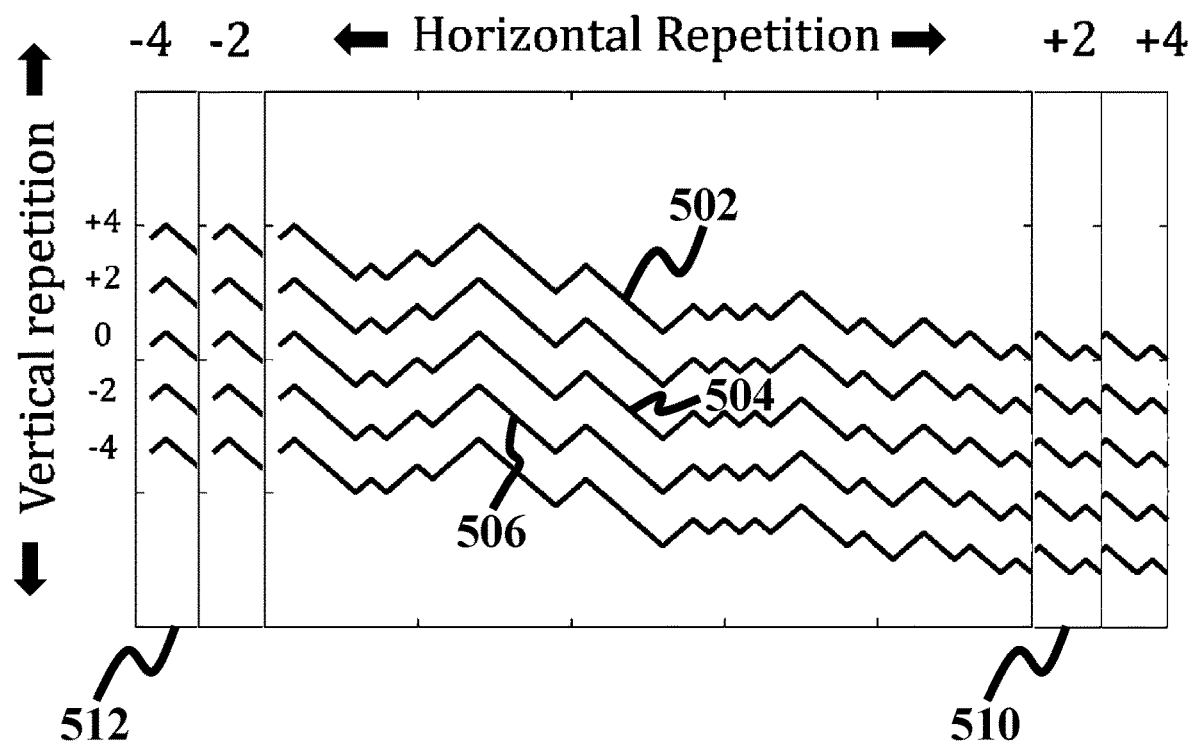
FIG. 5 shows a plurality of vertically repeated reference sequences and a plurality of horizontally repeated reference sequences, consistent with one or more exemplary embodiments of the present disclosure.

In further detail with respect to steps 116 and 118, FIG. 5 shows a plurality of vertically repeated reference sequences and a plurality of horizontally repeated reference sequences, consistent with one or more exemplary embodiments of the present disclosure. In an exemplary embodiment, each of the plurality of vertically repeated reference sequences may include a repetition of the optically coded reference sequence shifted in a vertical direction by a first vertical shift. For example, a vertically repeated reference sequence 502 includes a repetition of an optically coded reference sequence 504 shifted in the vertical direction by +4 pixels. As another example, a vertically repeated reference sequence 506 includes a repetition of optically coded reference sequence 504 shifted in the vertical direction by −2 pixels.

In an exemplary embodiment, each of the plurality of horizontally repeated reference sequences may include a repetition of one of the plurality of vertically repeated reference sequences shifted in a horizontal direction by a first horizontal shift. For example, each of horizontally repeated reference sequences 510 includes a repetition of the plurality of vertically repeated reference sequences shifted in the horizontal direction by +2 pixels. As another example, each of horizontally repeated reference sequences 512 includes a repetition of the plurality of vertically repeated reference sequences shifted in the horizontal direction by −4 pixels.

Figure 6:
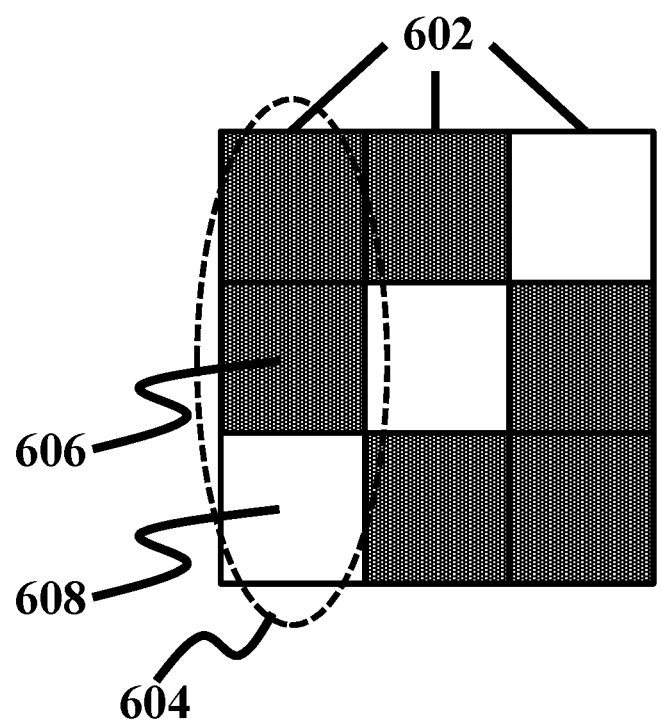
FIG. 6 shows a schematic of a first two-dimensional image, consistent with one or more exemplary embodiments of the present disclosure.

For further detail with regards to step 120, FIG. 6 shows a schematic of a first two-dimensional image 600, consistent with one or more exemplary embodiments of the present disclosure. In an exemplary embodiment, first two-dimensional image 600 may include a first plurality of columns 602 and each of first plurality of columns 602 may include a first vertical arrangement of pixels 604. In an exemplary embodiment, each pixel of first vertical arrangement of pixels 604 may include one of a dark pixel 606 or a bright pixel 608.

Figure 7:
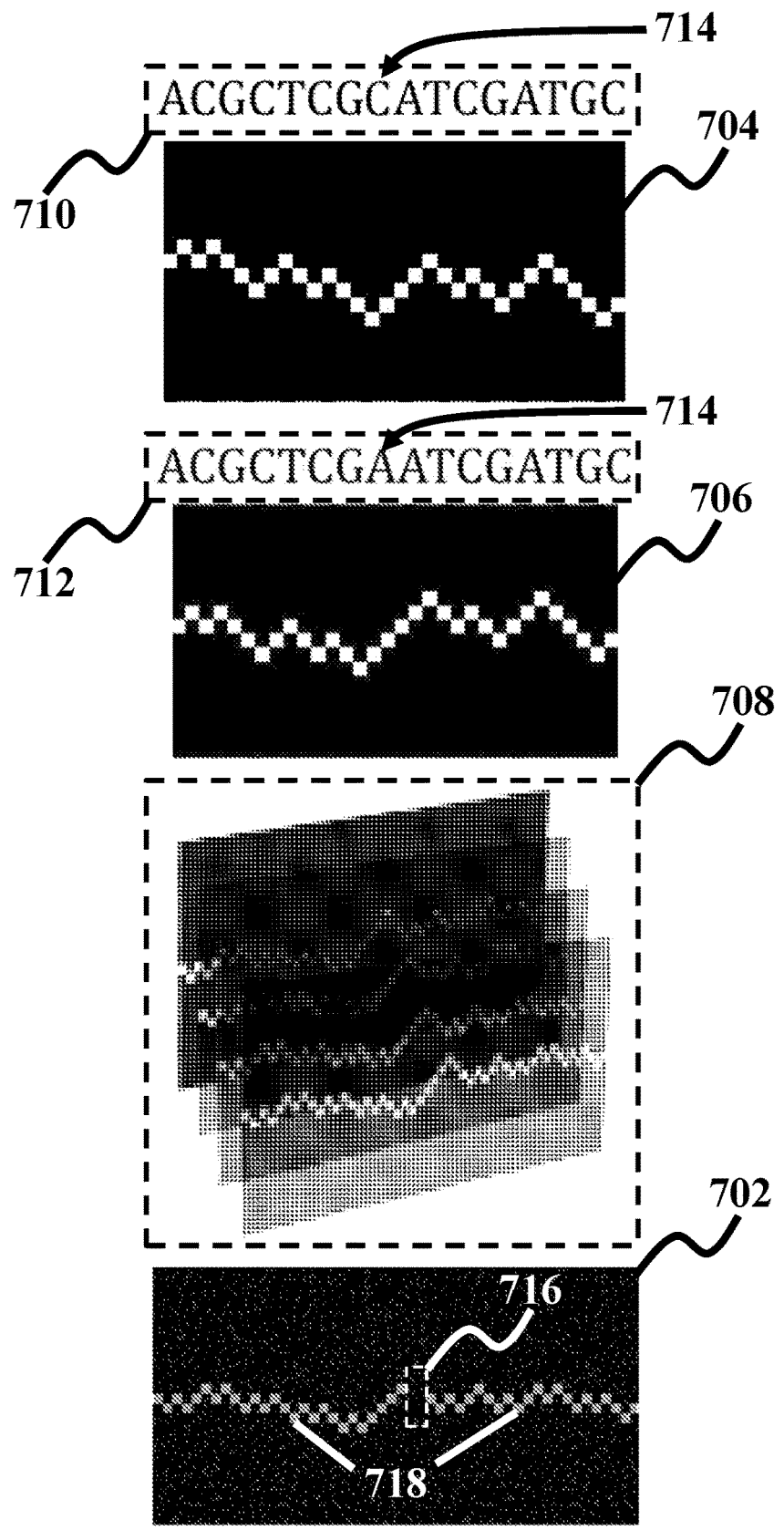
FIG. 7 shows generating a first two-dimensional image by overlapping an optically coded input sequence with an optically coded reference sequence and a plurality of vertically and horizontally repeated reference sequences, consistent with one or more exemplary embodiments of the present disclosure.

FIG. 7 shows generating a first two-dimensional image 702 by overlapping an optically coded input sequence 704 with an optically coded reference sequence 706 and a plurality of vertically and horizontally repeated reference sequences 708, consistent with one or more exemplary embodiments of the present disclosure. In an exemplary embodiment, optically coded input sequence 704 may be associated with an input sequence 710 (SEQ ID NO: 4) and optically coded reference sequence 706 may be associated with a reference sequence 712 (SEQ ID NO: 3). In an exemplary embodiment, a mutation may occur in a position 714 of input sequence 710 (SEQ ID NO: 4) and reference sequence 712 (SEQ ID NO: 3), in which element value A in reference sequence 712 (SEQ ID NO: 3) may be replaced with element value C in input sequence 710 (SEQ ID NO: 4). As a result, in an exemplary embodiment, a series of dark pixels 716 may appear between two strings of bright pixels 718 in first two-dimensional image 702, indicating a mutation in position 714.

Figure 8:
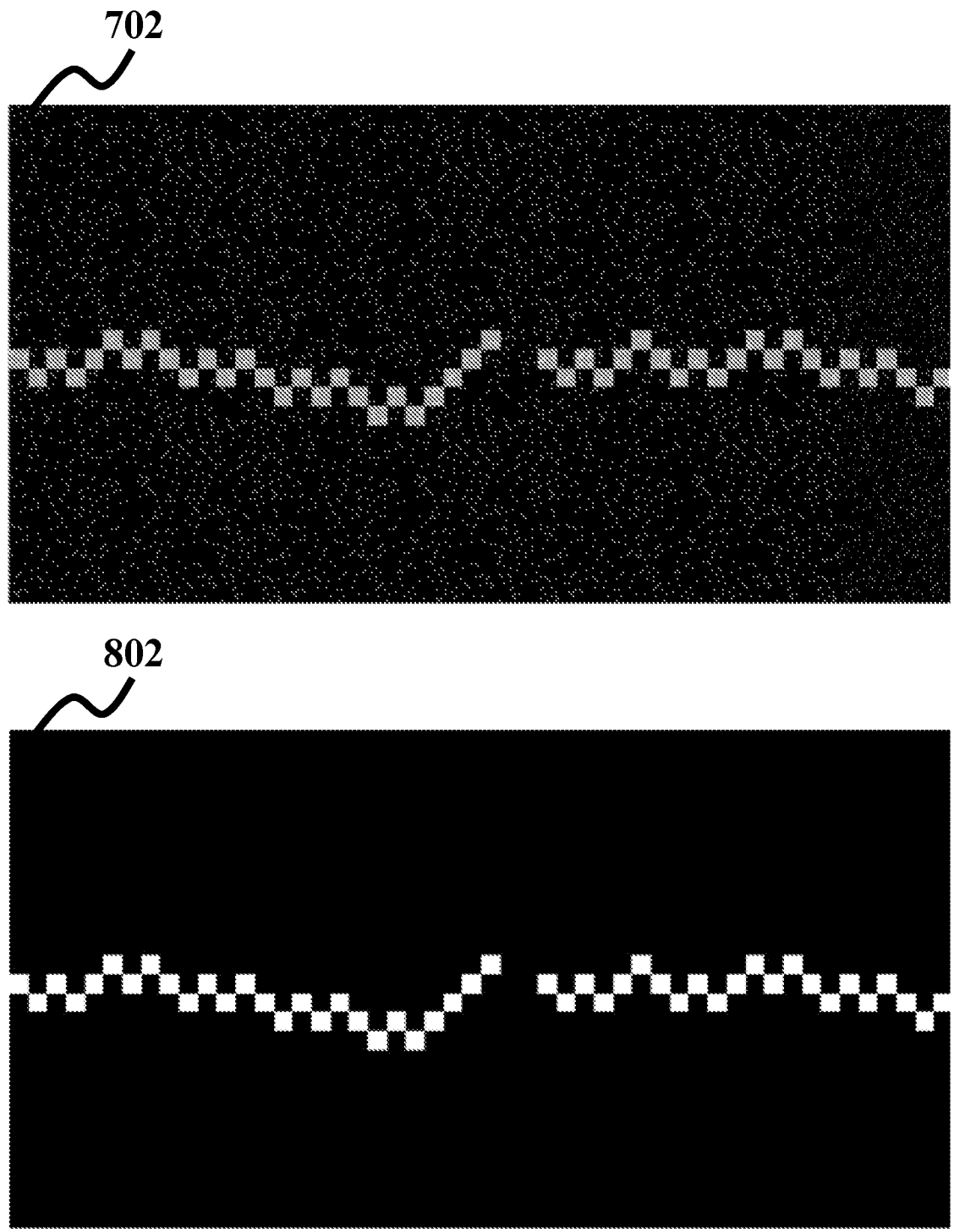
FIG. 8 shows generating a first optically thresholded two-dimensional image from a first two-dimensional image, consistent with one or more exemplary embodiments of the present disclosure.

For further detail with regards to step 122, FIG. 8 shows generating a first optically thresholded two-dimensional image 802 from first two-dimensional image 702, consistent with one or more exemplary embodiments of the present disclosure. In an exemplary embodiment, "thresholded image" may refer to an image in which each pixel may be replaced with a dark pixel if the brightness level of the respective pixel is lower than a given threshold. In an exemplary embodiment, generating first optically thresholded two-dimensional image 802 (step 122) may include replacing bright pixel 608 with dark pixel 606 in first vertical arrangement of pixels 604 responsive to detecting that a brightness level of bright pixel 608 is lower than a brightness threshold. In an exemplary embodiment, the brightness threshold may be determined according to an amplitude of a crosstalk noise, which may be generated during an optical implementation of method 100.

Figure 9:
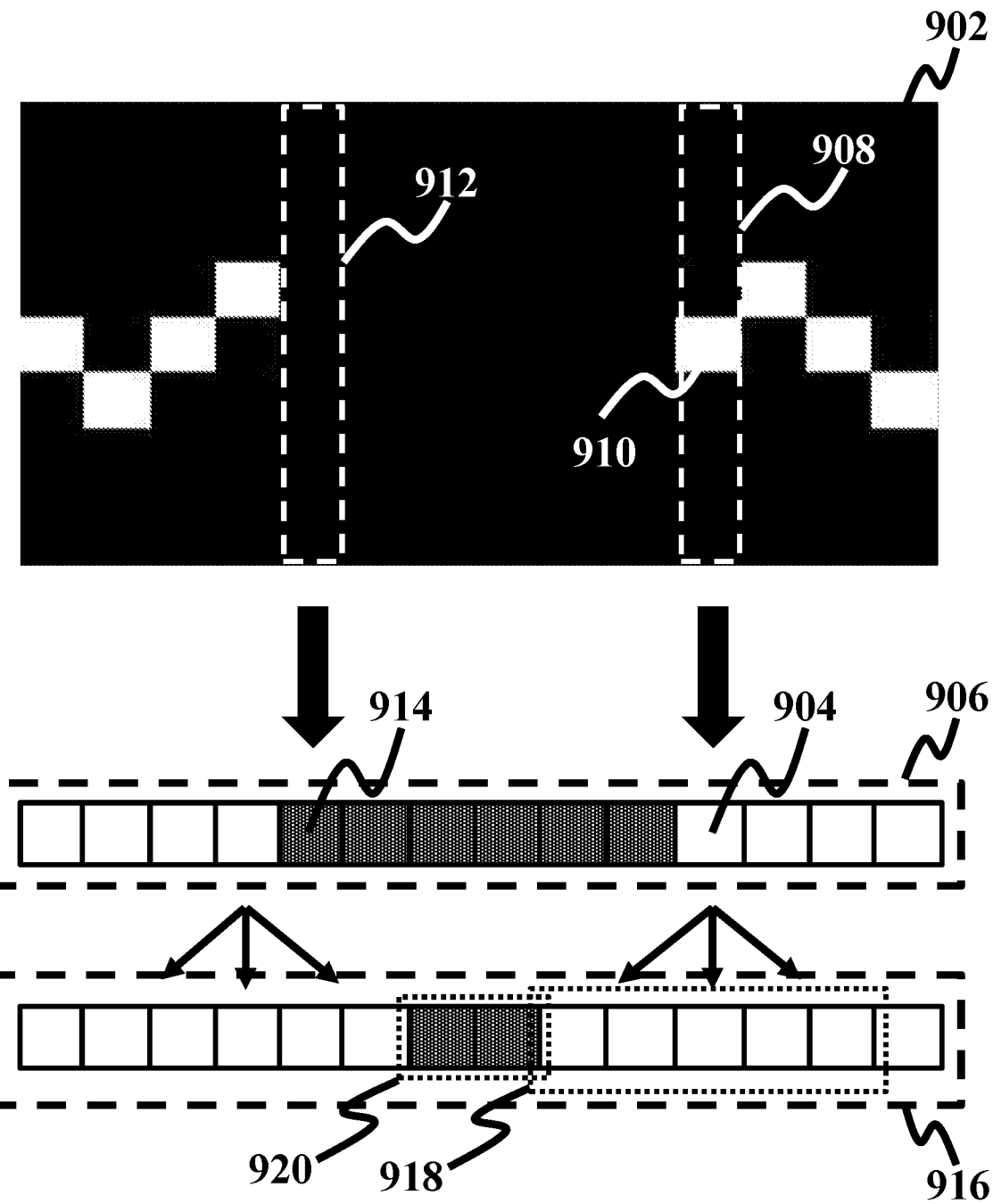
FIG. 9 shows generating a first one-dimensional image from a first optically thresholded two-dimensional image and extracting a first sequence of pixels from a first one-dimensional image, consistent with one or more exemplary embodiments of the present disclosure.

In further detail with respect to steps 124 and 126, FIG. 9 shows generating a first one-dimensional image from a first optically thresholded two-dimensional image 902 and extracting a first sequence of pixels from the first one-dimensional image, consistent with one or more exemplary embodiments of the present disclosure. In an exemplary embodiment, generating the first one-dimensional image (step 124) may include projecting a first column of first plurality of columns 602 into a first pixel of a first pixel array by including bright pixel 608 in the first pixel responsive to determining that the first column includes bright pixel 608. For example, a first pixel 904 of a first pixel array 906 may include bright pixel 608 since an associated first column 908 of first plurality of columns 602 includes bright pixel 608 at a position 910. As another example, a first column 912 may be projected into a first pixel 914 since there is no bright pixel in first column 912.

In an exemplary embodiment, coding of each element in the input sequence may be affected by its previous, as well as its next elements. Therefore, in the case of a mutation, coding of three consequent elements may be altered. In order to eliminate undesired zero points in the resultant aligned sequence, every bright pixel may be mapped to five neighboring pixels.

In an exemplary embodiment, extracting the first sequence of pixels (step 126) may include mapping the first pixel to a first neighboring pixels subset of the first pixel array responsive to including bright pixel 608 in the first pixel. For example, extracting first sequence of pixels 916 may include mapping first pixel 904 to a first neighboring pixels subset 918 of first pixel array 906, since first pixel 904 includes bright pixel 608. In an exemplary embodiment, the first neighboring pixels subset may include five successive pixels of the first pixel array with the first pixel at the center of the five successive pixels.

Referring again to FIGS. 1A, 2, and 9, in an exemplary embodiment, determining the mutation in input sequence 202 (SEQ ID NO: 1) (step 108) may include detecting a respective pair of successive dark pixels 920 in first sequence of pixels 916. In an exemplary embodiment, respective pair of successive dark pixels 920 may be associated with low-value element 210. In other words, in an exemplary embodiment, low-value element 210 in input sequence 202 (SEQ ID NO: 1) may be mapped to respective pair of successive dark pixels 920.

Figure 1D:
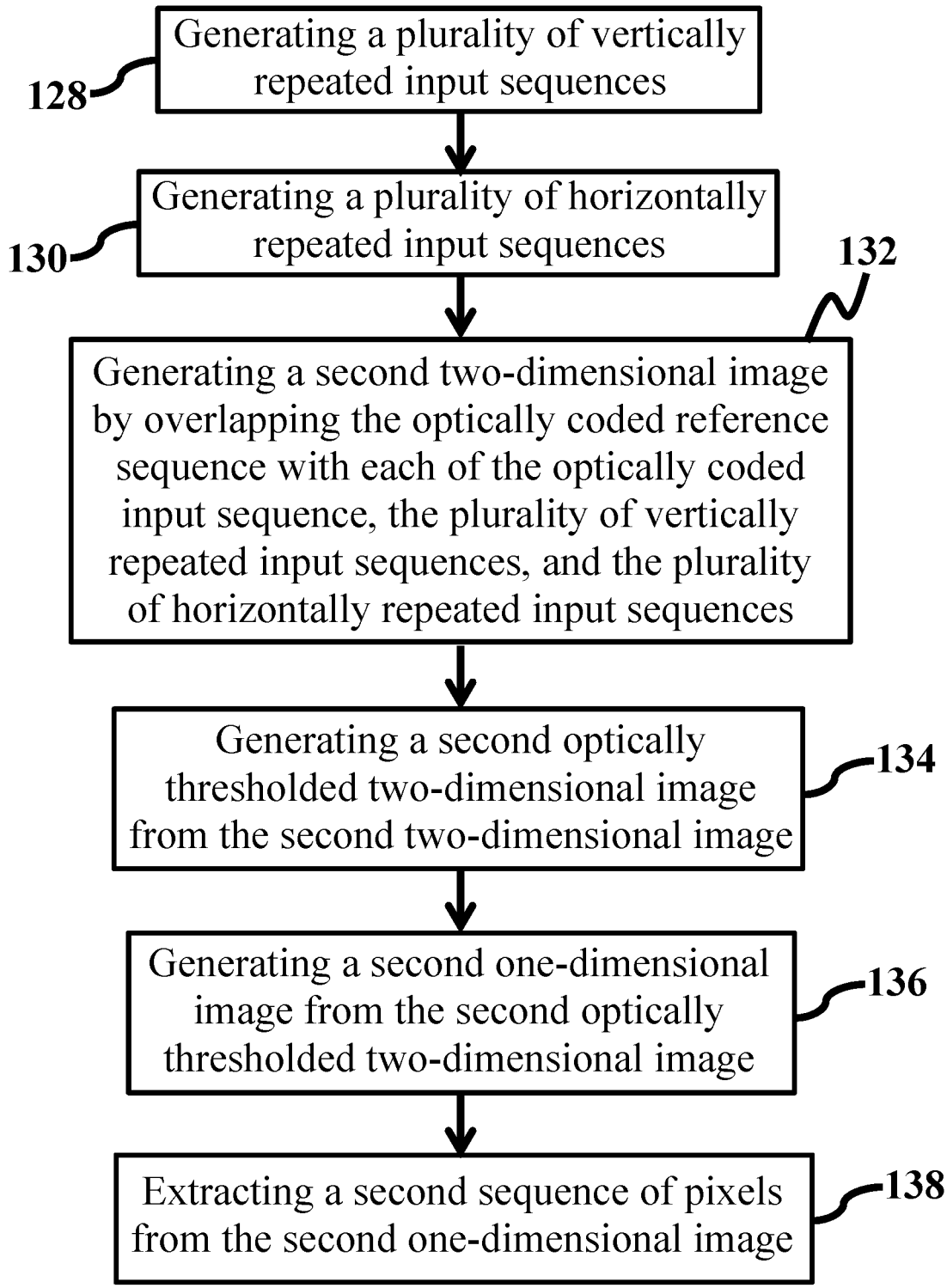
FIG. 1D shows a flowchart of additional steps for generating an aligned sequence, consistent with one or more exemplary embodiments of the present disclosure.

In further detail with regards to step 106, FIG. 1D shows a flowchart of additional steps for generating the aligned sequence, consistent with one or more exemplary embodiments of the present disclosure. In an exemplary embodiment, generating the aligned sequence (step 106) may further include generating a plurality of vertically repeated input sequences from the optically coded input sequence (step 128), generating a plurality of horizontally repeated input sequences from the plurality of vertically repeated reference sequences (step 130), generating a second two-dimensional image by overlapping the optically coded reference sequence with each of the optically coded input sequence, the plurality of vertically repeated input sequences, and the plurality of horizontally repeated input sequences (step 132), generating a second optically thresholded two-dimensional image from the second two-dimensional image (step 134), generating a second one-dimensional image from the second optically thresholded two-dimensional image (step 136), and extracting a second sequence of pixels from the second one-dimensional image (step 138). Each of the plurality of vertically repeated input sequences may include a repetition of the optically coded input sequence shifted in a vertical direction by a second vertical shift, and each of the plurality of horizontally repeated input sequences may include a repetition of one of the plurality of vertically repeated reference sequences shifted in a horizontal direction by a second horizontal shift. In an exemplary embodiment, the second two-dimensional image may include a second plurality of columns, and each of the second plurality of columns may include a second vertical arrangement of pixels. In an exemplary embodiment, each pixel of the second vertical arrangement of pixels may include one of the dark pixel or the bright pixel.

In an exemplary embodiment, generating the second optically thresholded two-dimensional image (step 132) may include replacing the bright pixel with the dark pixel in the second vertical arrangement of pixels responsive to detecting that a brightness level of the bright pixel is lower than the brightness threshold. In an exemplary embodiment, generating the second one-dimensional image (step 136) may include projecting a second column of the second plurality of columns into a second pixel of a second pixel array by including the bright pixel in the second pixel responsive to determining that the second column includes the bright pixel.

In an exemplary embodiment, extracting the second sequence of pixels (step 138) may include mapping the second pixel to a second neighboring pixels subset of the second pixel array responsive to including the bright pixel in the second pixel. Further details of steps 128-138 may be similar to those of steps 116-126 discussed above. Specifically, step 128 may be similar to step 116, step 130 may be similar to step 118, step 132 may be similar to step 120, step 134 may be similar to step 122, step 136 may be similar to step 124, and step 138 may be similar to step 126.

Figure 1E:
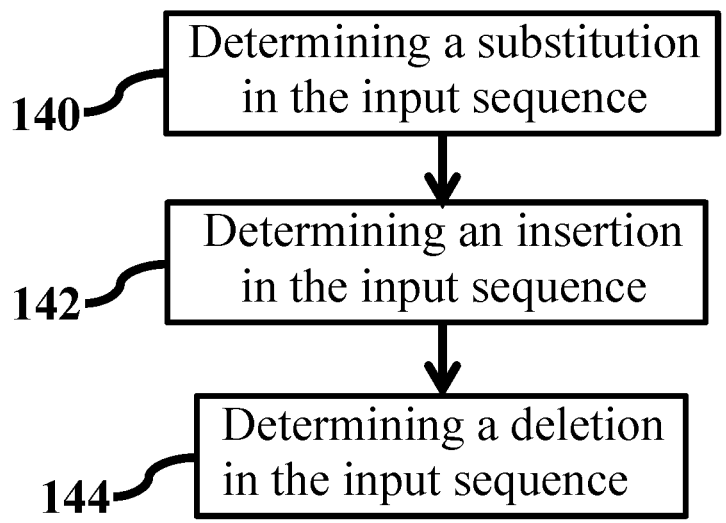
FIG. 1E shows a flowchart for determining mutation in an input sequence, consistent with one or more exemplary embodiments of the present disclosure.

For further detail with regards to step 108, FIG. 1E shows a flowchart for determining mutation in the input sequence, consistent with one or more exemplary embodiments of the present disclosure. In an exemplary embodiment, determining mutation in the input sequence (step 108) may include determining a substitution in the input sequence by detecting a first pair of successive dark pixels in the first sequence of pixels and detecting a second pair of successive dark pixels in the second sequence of pixels (step 140), determining an insertion in the input sequence by detecting a third pair of successive dark pixels in the first sequence of pixels and detecting a fourth pair of successive bright pixels in the second sequence of pixels (step 142), and determining a deletion in the input sequence by detecting a fifth pair of successive bright pixels in the first sequence of pixels and detecting a sixth pair of successive dark pixels in the second sequence of pixels (step 144).

Figure 10:
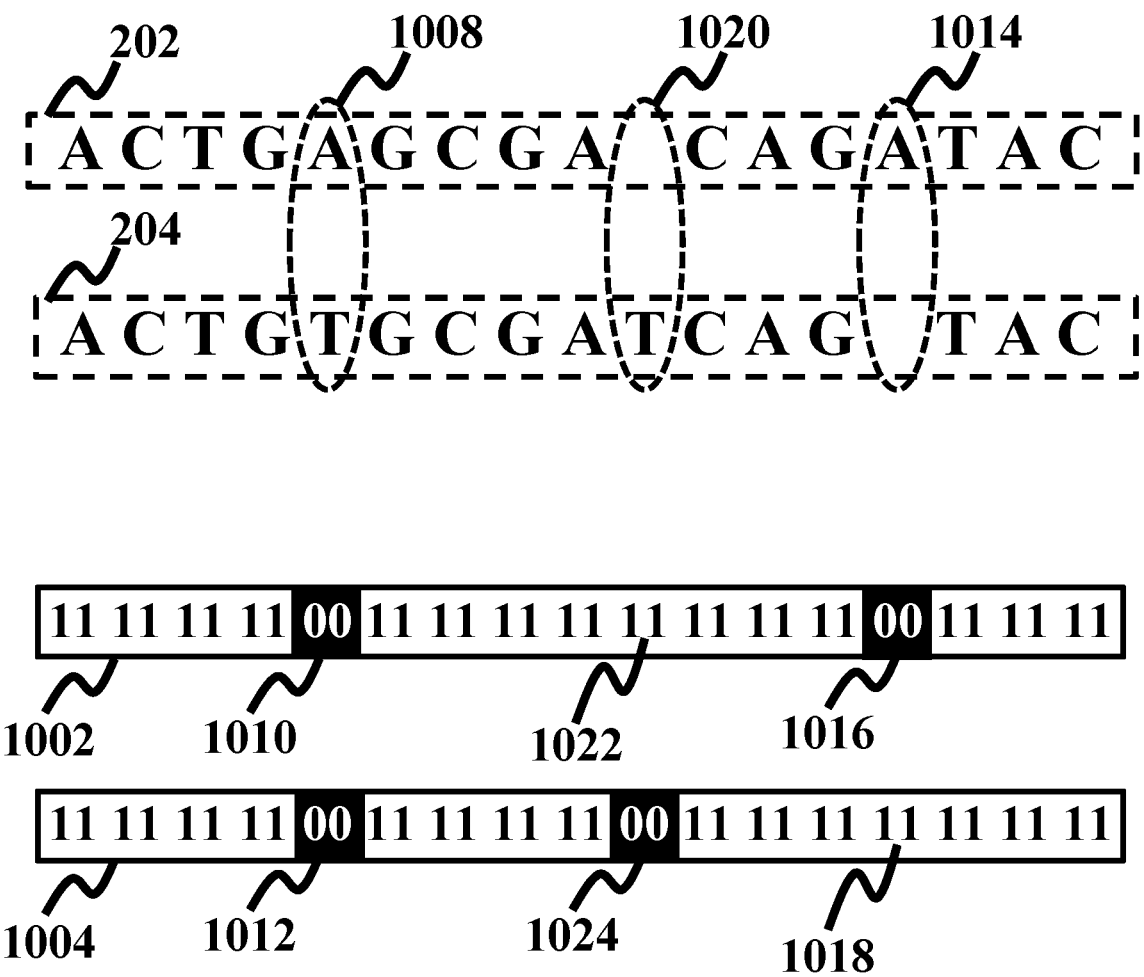
FIG. 10 shows a first sequence of pixels and a second sequence of pixels extracted from an input sequence and a reference sequence, consistent with one or more exemplary embodiments of the present disclosure.

For further detail with regards to steps 140-144, FIG. 10 shows a first sequence of pixels 1002 and a second sequence of pixels 1004 extracted from input sequence 202 (SEQ ID NO: 1) and reference sequence 204 (SEQ ID NO: 2), consistent with one or more exemplary embodiments of the present disclosure. In an exemplary embodiment, determining a substitution 1008 in input sequence 202 (SEQ ID NO: 1) (in which T in reference sequence 204 (SEQ ID NO: 2) is substituted by A in input sequence 202 (SEQ ID NO: 1)) in step 140 may include detecting a first pair 1010 of successive dark pixels in first sequence of pixels 1002 and detecting a second pair of successive dark pixels 1012 in second sequence of pixels 1004. In an exemplary embodiment, first pair 1010 may be associated with second pair 1012, and each of first pair 1010 and second pair 1012 may be associated with the low-value element (represented by '00' in first sequence of pixels 1002 and second sequence of pixels 1004). In an exemplary embodiment, first pair 1010 and second pair 1012 may appear in their respective sequences at positions corresponding to substitution 1008.

In an exemplary embodiment, determining an insertion 1014 in input sequence 202 (SEQ ID NO: 1) (in which A is inserted in input sequence 202 (SEQ ID NO: 1)) in step 142 may include detecting a third pair 1016 of successive dark pixels in first sequence of pixels 1002 and detecting a fourth pair 1018 of successive bright pixels in second sequence of pixels 1018. In an exemplary embodiment, third pair 1016 may be associated with fourth pair 1018. In an exemplary embodiment, third pair 1016 and fourth pair 1018 may appear in their respective sequences at positions corresponding to insertion 1014. In an exemplary embodiment, third pair 1016 may be associated with the low-value element and fourth pair 1018 may be associated with the high-value element (represented by "11" in second sequence of pixels 1004).

In an exemplary embodiment, determining a deletion 1020 in input sequence 202 (SEQ ID NO: 1) (in which T is deleted from input sequence 202 (SEQ ID NO: 1)) in step 144 may include detecting a fifth pair 1022 of successive bright pixels in first sequence of pixels 1002 and detecting a sixth pair 1024 of successive dark pixels in second sequence of pixels 1004. In an exemplary embodiment, fifth pair 1022 may be associated with sixth pair 1024. In an exemplary embodiment, fifth pair 1022 and sixth pair 1024 may appear in their respective sequences at positions corresponding to deletion 1020. In an exemplary embodiment, fifth pair 1022 may be associated with the high-value element and the sixth pair 1024 may be associated with the low-value element.

Figure 11:
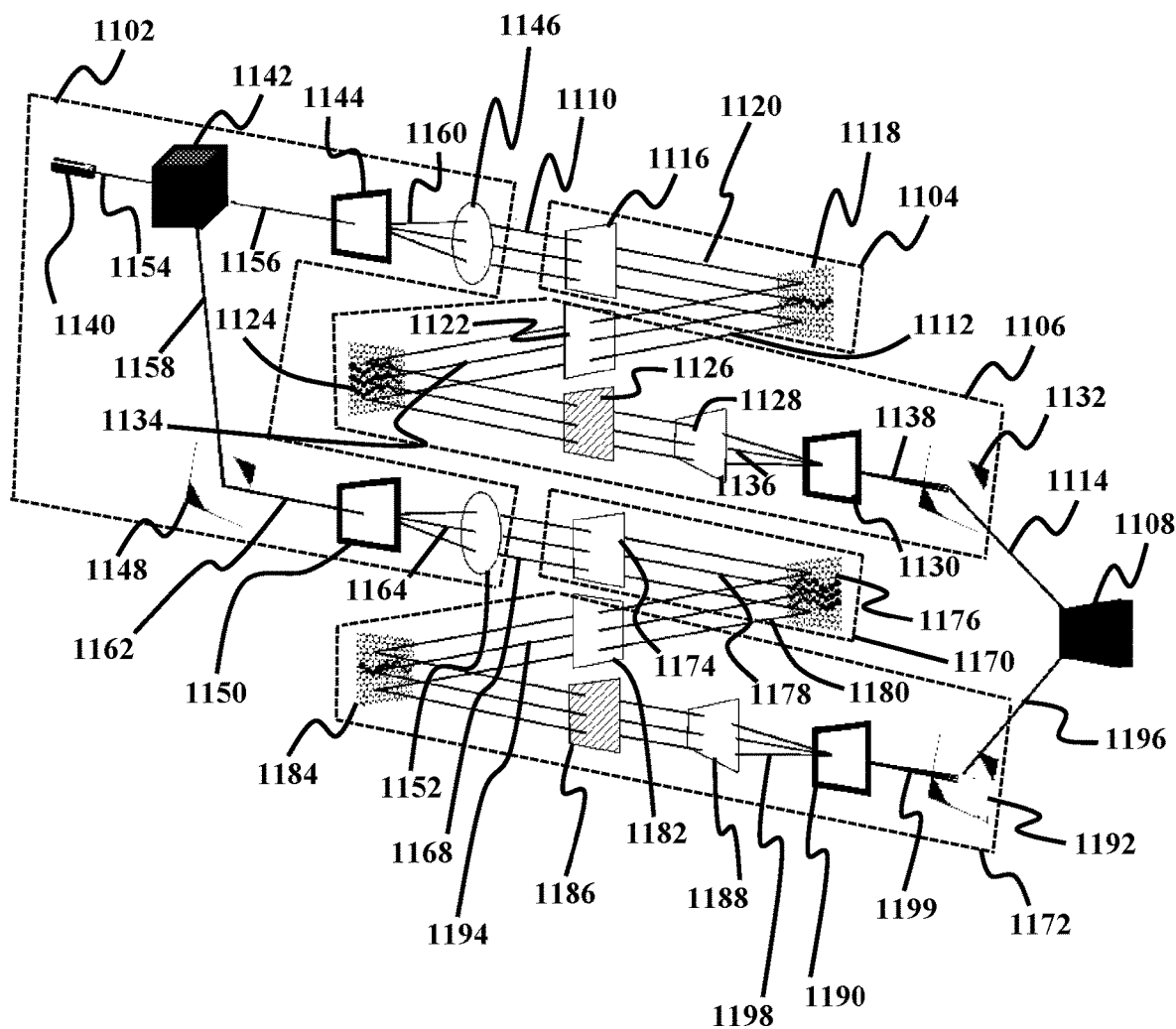
FIG. 11 shows a schematic of a system for optically detecting mutations in a sequence of DNA, consistent with one or more exemplary embodiments of the present disclosure.

FIG. 11 shows a schematic of a system for optically detecting mutations in a sequence of DNA, consistent with one or more exemplary embodiments of the present disclosure. In an exemplary embodiment, different steps of method 100 may be implemented by utilizing an exemplary system 1100. In an exemplary embodiment, system 1100 may include a light source 1102, a first optical filter 1104, a second optical filter 1106, and a detector 1108. In an exemplary embodiment, light source 1102 may be configured to illuminate an input optical signal 1110. In an exemplary embodiment, first optical filter 1104 may be configured to generate an optically coded input signal 1112 from input optical signal 1110 based on an input sequence, similar to input sequence 202 (SEQ ID NO: 1). The exemplary input sequence may include an input arrangement of a plurality of elements, and each of the plurality of elements may include an element value of a plurality of element values. In an exemplary embodiment, each element value may include one of adenine (A), guanine (G), thymine (T), and cytosine (C).

In an exemplary embodiment, second optical filter 1106 may be configured to generate an aligned signal 1114 by overlapping optically coded input signal 1112 with a reference sequence, similar to reference sequence 204 (SEQ ID NO: 2). In an exemplary embodiment, the reference sequence may include a reference arrangement of the plurality of elements. In an exemplary embodiment, detector 1108 may be configured to receive and display aligned signal 1114.

In an exemplary embodiment, first optical filter 1104 may include a first polarizer 1116 and a first electrically tunable color filter 1118. In an exemplary embodiment, first polarizer 1116 may be configured to generate a polarized input signal 1120 from input optical signal 1110. In an exemplary embodiment, first electrically tunable color filter 1118 may be configured to generate a primary coded input signal from polarized input signal 1120 by overlapping polarized input signal 1120 with a first arrangement of plurality of bright-pixels patterns 302 on first electrically tunable color filter 1118 and generate optically coded input signal 1112 from the primary coded input signal by modifying a wavelength of an element of the primary coded input signal based on neighboring elements of a corresponding element in the input sequence. In an exemplary embodiment, the first arrangement may correspond to the input arrangement.

In an exemplary embodiment, second optical filter 1106 may include a second polarizer 1122, a second electrically tunable color filter 1124, a first optical thresholder 1126, a first cylindrical lens 1128, a first diffraction grating 1130, and a first mirror 1132. In an exemplary embodiment, second polarizer 1122 may be configured to generate a polarized coded input signal 1134 from optically coded input signal 1112. In an exemplary embodiment, second electrically tunable color filter 1124 may be configured to generate a first primary image from polarized coded input signal 1134 by overlapping polarized coded input signal 1134 with each of a second arrangement of plurality of bright-pixels patterns 302 on second electrically tunable color filter 1124, a first plurality of vertical arrangements of plurality of bright-pixels patterns 302 on the second electrically tunable color filter, and a first plurality of horizontal arrangements of plurality of bright-pixels patterns 302 on second electrically tunable color filter 1124, and generate the first two-dimensional image from the first primary image by modifying a wavelength of each element of the first primary image based on neighboring elements of a corresponding element in the reference sequence. In an exemplary embodiment, the second arrangement may correspond to the reference arrangement. In an exemplary embodiment, each of the first plurality of vertical arrangements may include a repetition of the second arrangement shifted in the vertical direction of second electrically tunable color filter 1124 by the first vertical shift, and each of the first plurality of horizontal arrangements may include a repetition of one of the first plurality of vertical arrangements shifted in the horizontal direction of second electrically tunable color filter 1124 by the first horizontal shift, as illustrated in FIG. 5.

In an exemplary embodiment, first optical thresholder 1126 may be configured to generate the first optically thresholded two-dimensional image from the first two-dimensional image by blocking an illumination of bright pixel 608 responsive to detecting that the brightness level of bright pixel 608 is lower than the brightness threshold. In an exemplary embodiment, first cylindrical lens 1128 may be configured to generate the first one-dimensional image from the first optically thresholded two-dimensional image by projecting the first column of the first plurality of columns into the first pixel of the first pixel array.

In an exemplary embodiment, first diffraction grating 1130 may be configured to receive an illumination of the first one-dimensional image and generate a first segment of the aligned signal. In an exemplary embodiment, the illumination of the first one-dimensional image may include a first plurality of rays 1136 and each of first plurality of rays 1136 may be associated with bright pixel 608. In an exemplary embodiment, first diffraction grating 1130 may be configured to generate the first segment of the aligned signal by diffracting each of first plurality of rays 1136 into a first plurality of diffracted rays 1138. In an exemplary embodiment, first plurality of diffracted rays 1138 may be associated with the first neighboring pixels subset of the first pixel array responsive to including bright pixel 608 in the first pixel. In an exemplary embodiment, first mirror 1132 may be configured to reflect the first segment on detector 1108.

In an exemplary embodiment, light source 1102 may include a laser 1140, a beam splitter 1142, a second diffraction grating 1144, a first optical lens 1146, a second mirror 1148, a third diffraction grating 1150, and a second optical lens 1152. In an exemplary embodiment, laser 1140 may be configured to emit a beam 1154 of light. In an exemplary embodiment, beam splitter 1142 may be configured to split beam 1154 into a first split beam 1156 and a second split beam 1158. In an exemplary embodiment, second diffraction grating 1144 may be configured to diffract first split beam 1156 into a first plurality of diffracted beams 1160. In an exemplary embodiment, first optical lens 1146 may be configured to generate input optical signal 1110 by producing a first plurality of parallel beams from first plurality of diffracted beams 1160. In an exemplary embodiment, second mirror 1148 may be configured to produce a reflection 1162 of second split beam 1158. In an exemplary embodiment, third diffraction grating 1150 may be configured to diffract reflection 1162 of second split beam 1158 into a second plurality of diffracted beams 1164. In an exemplary embodiment, second optical lens 1152 may be configured to generate a reference optical signal 1168 by producing a second plurality of parallel beams from second plurality of diffracted beams 1164.

In an exemplary embodiment, system 1100 may further include a third optical filter 1170 and a fourth optical filter 1172. In an exemplary embodiment, third optical filter 1170 may include a third polarizer 1174 and a third electrically tunable color filter 1176. In an exemplary embodiment, third polarizer 1174 may be configured to generate a polarized reference signal 1178 from reference optical signal 1168. In an exemplary embodiment, third electrically tunable color filter 1176 may be configured to generate a primary coded reference signal from polarized reference signal 1178 by overlapping polarized reference signal 1178 with a third arrangement of plurality of bright-pixels patterns 302 on third electrically tunable color filter 1176 and generate an optically coded reference signal 1180 from the primary coded reference signal by modifying a wavelength of each element of the primary coded reference signal based on neighboring elements of a corresponding element in the reference sequence. In an exemplary embodiment, the third arrangement may correspond to the reference arrangement.

In an exemplary embodiment, fourth optical filter 1172 may include a fourth polarizer 1182, a fourth electrically tunable color filter 1184, a second optical thresholder 1186, a second cylindrical lens 1188, a fourth diffraction grating 1190, and a third mirror 1192. In an exemplary embodiment, fourth polarizer 1182 may be configured to generate a polarized coded reference signal 1194 from optically coded reference signal 1180 based on the input arrangement. In an exemplary embodiment, fourth electrically tunable color filter 1184 may be configured to generate a second primary image from polarized coded reference signal 1194 by overlapping polarized coded reference signal 1194 with each of a fourth arrangement of plurality of bright-pixels patterns 302 on fourth electrically tunable color filter 1184, a second plurality of vertical arrangements of plurality of bright-pixels patterns 302 on fourth electrically tunable color filter 1184, and a second plurality of horizontal arrangements of plurality of bright-pixels patterns 302 on fourth electrically tunable color filter 1184, and generate the second two-dimensional image from the second primary image by modifying a wavelength of an element of the second primary image based on neighboring elements of a corresponding element in the input sequence. In an exemplary embodiment, the fourth arrangement may correspond to the input arrangement of the plurality of elements. In an exemplary embodiment, each of the second plurality of vertical arrangements may include a repetition of the fourth arrangement shifted in the vertical direction of fourth electrically tunable color filter 1184 by the second vertical shift, and each of the second plurality of horizontal arrangements may include a repetition of one of the second plurality of vertical arrangements shifted in the horizontal direction of fourth electrically tunable color filter 1184 by the second horizontal shift, similar to the illustration of FIG. 5.

In an exemplary embodiment, second optical thresholder 1186 may be configured to generate the second optically thresholded two-dimensional image from the second two-dimensional image by blocking an illumination of bright pixel 608 responsive to detecting that the brightness level of the bright pixel is lower than the brightness threshold. In an exemplary embodiment, second cylindrical lens 1188 may be configured to generate the second one-dimensional image from the second optically thresholded two-dimensional image by projecting the second column of the second plurality of columns into the second pixel of the second pixel array.

In an exemplary embodiment, fourth diffraction grating 1190 may be configured to receive an illumination of the second one-dimensional image and generate a second segment 1196 of the aligned signal. In an exemplary embodiment, the illumination of the second one-dimensional image may include a second plurality of rays 1198, and each of second plurality of rays 1198 may be associated with bright pixel 608. In an exemplary embodiment, fourth diffraction grating 1190 may be configured to generate second segment 1196 of the aligned signal by diffracting each of second plurality of rays 1198 into a second plurality of diffracted rays 1199. In an exemplary embodiment, second plurality of diffracted rays 1199 may be associated with the second neighboring pixels subset of the second pixel array responsive to including bright pixel 608 in the second pixel. In an exemplary embodiment, third mirror 1192 may be configured to reflect second segment 1196 on detector 1108.

Figure 12:
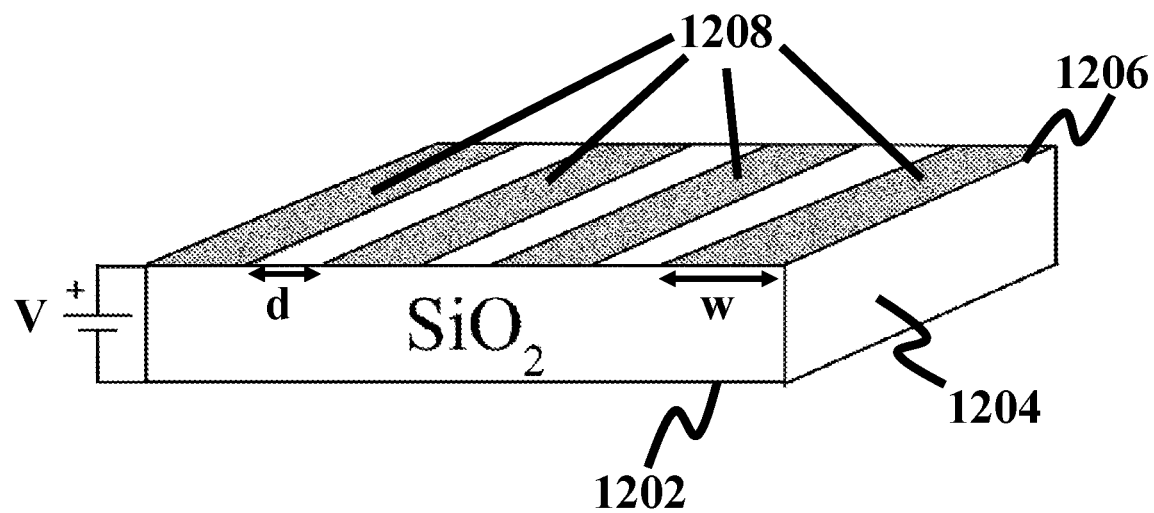
FIG. 12 shows a schematic of a graphene-based spatial light modulator, consistent with one or more exemplary embodiments of the present disclosure.

FIG. 12 shows a schematic of a graphene-based spatial light modulator 1200, consistent with one or more exemplary embodiments of the present disclosure. In an exemplary embodiment, each of first optical filter 1104, second optical filter 1106, third optical filter 1170, and fourth optical filter 1172 may include a plurality of graphene-based spatial light modulators. Each of the plurality of graphene-based spatial light modulators may be analogous to graphene-based spatial light modulator 1200. In an exemplary embodiment, graphene-based spatial light modulator 1200 may be configured to prevent transmission of a light beam associated with a wavelength range responsive to a voltage V applied to graphene-based spatial light modulator 1200. In an exemplary embodiment, graphene-based spatial light modulator 1200 may include a conductive layer 1202, a dielectric layer 1204 mounted on conductive layer 1202, and a graphene layer 1206 mounted on dielectric layer 1204. In an exemplary embodiment, graphene layer 1206 may include a plurality of parallel graphene sheets 1208.

In an exemplary embodiment, conductive layer 1202 may include a gold nanostructure. In an exemplary embodiment, dielectric layer 1204 may include a silicon dioxide material. In an exemplary embodiment, a space d between each adjacent graphene sheets of plurality of parallel graphene sheets 1208 may lie in a range of about 95 nm and about 105 nm. In an exemplary embodiment, a width w of each of plurality of parallel graphene sheets 1208 may lie in a range of about 195 nm and about 205 nm.

Example 1

In this example, assigning a wavelength to an exemplary DNA sequence according to Equation (1) is demonstrated. FIG. 13 shows a DNA sequence (SEQ ID NO: 5), consistent with one or more exemplary embodiments of the present disclosure. As shown in FIG. 13, nucleotide A is encoded with C as its previous nucleotide and G as its next nucleotide with a modulation wavelength of 458 nm based on Equation (1) with $k_{A,C}=2$, $k_{A,G}=3$, S=2, and R=1. On the other hand, a modulation wavelength of a first occurrence of nucleotide G with nucleotides T and G as its previous and next nucleotides, respectively, is 614 nm. For a first repetition of nucleotide G, with G as its previous and next nucleotides, R=1. Hence, according to Equation (1), the modulation wavelength is chosen as 630 nm; whereas for the second and third contiguous repetitions of G, with the same previous and next nucleotides, it is chosen as 632 nm and 634 nm.

Example 2

In this example, performance of an exemplary implementation of method 100 is evaluated. Two main scenarios are considered. In the first scenario, single base pair mutations, such as a single insertion, deletion, or substitution are considered because of the importance of single base pair detection required for disease diagnosing. In the second scenario, a multi-base pair mutation is considered to evaluate the ability of method 100 in detecting and locating various mutation types. Functionality and accuracy of exemplary implementations of method 100 and system 1100 are numerically evaluated using the commercially available software package LUMERICAL FDTD.

Two 150-element DNA sequences are compared with each other utilizing an exemplary implementation of method 100. Two DNA sequences, i.e., an exemplary reference DNA sequence (SEQ ID NO: 6) and an exemplary input DNA sequence (SEQ ID NO: 7), which include both single and multiple mutations, are as follow; including a single substitution, a single deletion, a single insertion, a multiple substitution, a multiple deletion, and a multiple insertion:
Input DNA sequence (SEQ ID NO: 7)=AGTTTGGCTCCTG
G̲CAGCCTCCATAAAATCTGGGACCCGAGCCCCACT GAGAGGT ACAGGCTGG A̲CCCTGTCTCGTAATGCAGCTCGGTTAGCACAGGG GCA̲ATGATGTG ACAGGCTGTGGTTCCGTAACCTCCTG TAT̲TCTCAAGCATG
Reference DNA sequence (SEQ ID NO: 6)=AGTTTGGCTCCTG T̲CAGCCTCCATAAAATCTGGGACCC A̲AGAGCCCCACTGAGAG GTA- CAGGCTGGCCCTGTCTCGTAATGCAGCTCGGT- TAGCACAGGGGCTGATGTGA CAGGCTGT A̲GGTTCCGTAACCTCCTGCC̲ATCTCAAGCATG The corresponding DNA sequences are optically coded by an exemplary implementation of method 100. For this purpose, each sequence element is coded in two horizontal pixels. Hence, representing each DNA string requires 300 pixels in the horizontal direction. Assuming a uniform distribution of A/C/G/T elements through the DNA string, at most 120 pixels are required in the vertical direction. Therefore, a 2D image of 120×300 pixels is produced for each of the input and reference DNA sequences.

Next, corresponding 2D images of the reference and input sequences, are repeated in the vertical and the horizontal directions. The number of sequence repetitions in either of the above, below, left, and right of the main sequence is set to 10.

Figure 14:
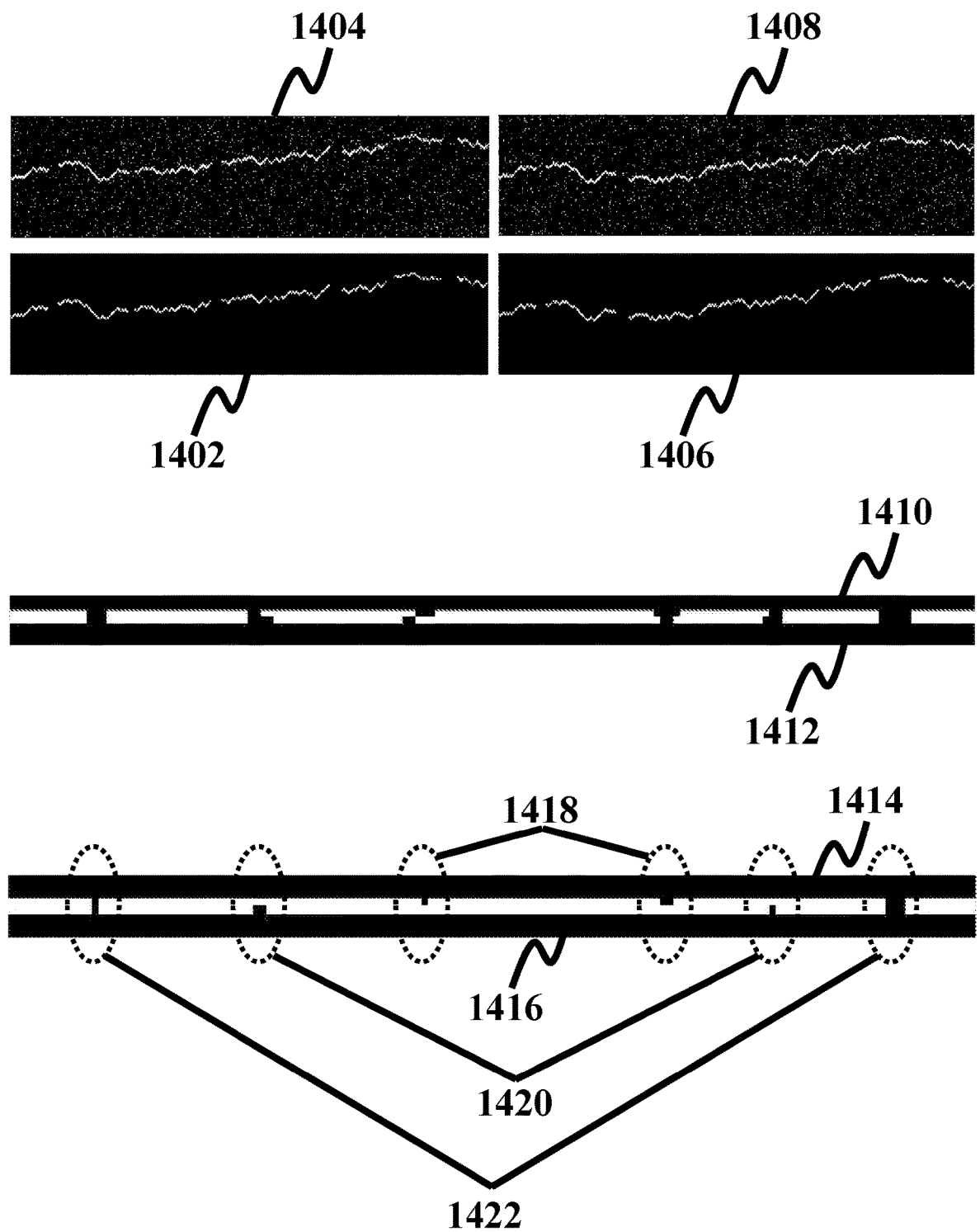
FIG. 14 shows resultant images of mutation detection, consistent with one or more exemplary embodiments of the present disclosure.

FIG. 14 shows resultant images of mutation detection, consistent with one or more exemplary embodiments of the present disclosure. An exemplary first optically thresholded two-dimensional image 1402 is generated from an exemplary first two-dimensional image 1404, and an exemplary second optically thresholded two-dimensional image 1406 is generated from an exemplary second two-dimensional image 1408. As illustrated in FIG. 14, traversing the images from left to right, the continuous line represents exact matching of the two DNA sequences, whereas each gap represents either single or multiple mutations.

Next, first optically thresholded two-dimensional image 1402 and second optically thresholded two-dimensional image 1406 are fed to optical cylindrical lenses to present a simple and more accurate result. Passing through a cylindrical lens produces a 1×300 pixel image. Therefore, two 1×300 pixel lines 1410 and 1412 are produced, which are fed to an exemplary diffraction grating with a diffraction order of two to map each bright pixel to five bright pixels in a row in parallel, leading to pixel lines 1414 and 1416. Comparing pixel lines 1414 and 1416 shows insertions 1418, deletions 1420, and substitutions 1422 in the input DNA sequence with respect to the reference DNA sequence.

Figure 15:
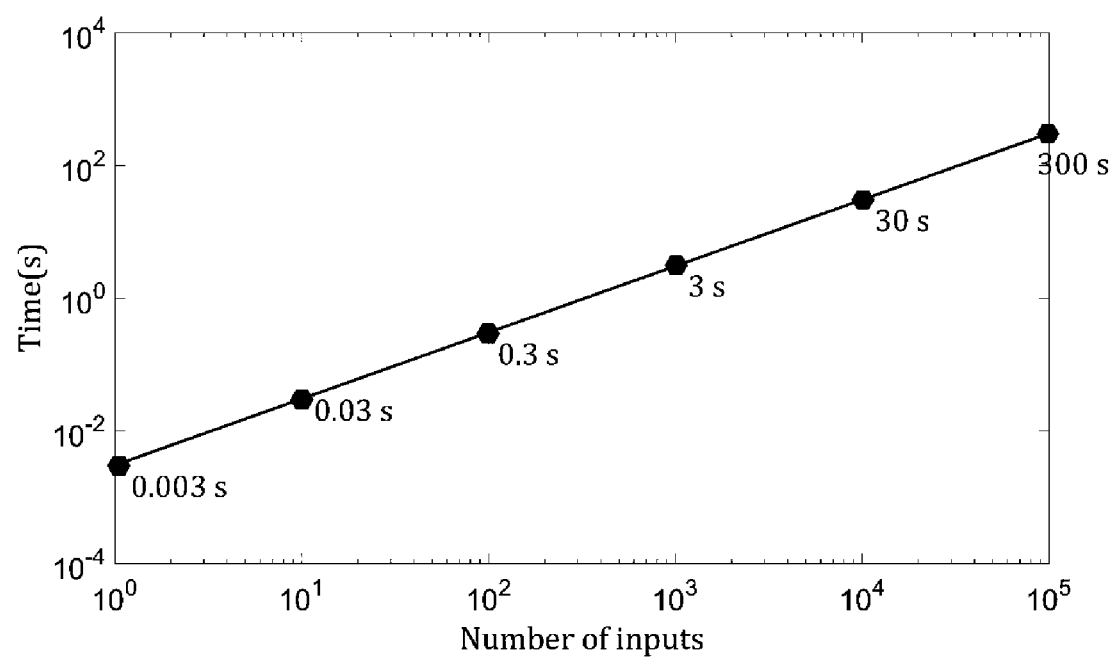
FIG. 15 shows an execution time of a method for mutation detection on for different number of elements in an input sequence, consistent with one or more exemplary embodiments of the present disclosure.

To validate an exemplary implementation of system 1100, different elements of system 1100 are simulated in LUMERICAL FDTD. For this purpose, a graphene-based color filter including a plurality of graphene sheets, a silver layer, and a dielectric is simulated. An exemplary graphene sheet model is based on a surface conductivity of graphene. A conductivity scale of two is used for the graphene model to account for two layers of graphene sheets used in the simulation. To implement the dielectric, a simple model with a constant refractive index of 1.9 is used, and the silver is assumed to be of perfect electric conductor boundary condition. Moreover, an exemplary SLM output is modeled by calculating electric field in front of the graphene based color filter at a corresponding wavelength range. A wavelength of color filter output is determined by an applied polarization to an incident electric field. FIG. 15 shows an execution time of an exemplary implementation of method 100 on an exemplary implementation of system 1100 for different number of elements in an input sequence, consistent with one or more exemplary embodiments of the present disclosure.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for optically detecting mutations in a sequence of DNA, the method comprising:
   generating an optically coded input sequence by optically coding an input sequence, the input sequence comprising an input arrangement of a plurality of elements, each of the plurality of elements comprising an element value of a plurality of element values;
   generating an optically coded reference sequence by optically coding a reference sequence, the reference sequence comprising a reference arrangement of the plurality of elements;
   generating an aligned sequence by overlapping the optically coded input sequence with the optically coded reference sequence, each element of the aligned sequence comprising one of a low-value element or a high-value element; and
   determining a mutation in the input sequence with respect to the reference sequence responsive to detecting the low-value element in the aligned sequence.

2. The method of claim 1, wherein optically coding the input sequence comprises:
   assigning a bright-pixels pattern of a plurality of bright-pixels patterns to each of the plurality of elements, the bright-pixels pattern comprising a sequence of bright pixels;
   generating a primary coded input sequence by arranging the plurality of bright-pixels patterns according to the input arrangement; and
   assigning a wavelength to an element of the primary coded input sequence based on neighboring elements of a corresponding element in the input sequence.

3. The method of claim 2, wherein assigning the bright-pixels pattern to each of the plurality of elements comprises assigning a respective pair of successive bright pixels to each of the plurality of elements, the respective pair of successive bright pixels associated with a dual-vector (DV)-curve representation of a respective element value of the plurality of element values.

4. The method of claim 2, wherein optically coding the reference sequence comprises:
   generating a primary coded reference sequence by arranging the plurality of bright-pixels patterns according to the reference arrangement; and
   assigning the wavelength to an element of the primary coded reference sequence based on neighboring elements of a corresponding element in the reference sequence.

5. The method of claim 4, assigning the wavelength to each of the elements of the primary coded input sequence and the primary coded reference sequence comprises assigning a wavelength $W_{N_i}$ to an $N_i^{th}$ element value of the plurality of element values according to an operation defined by the following:

$$W_{N_i} = w_{N_i} - (4 \times S \times k_{N_i, N_i-1}) - S \times k_{N_i, N_i+1} + S(R-1),$$

where:
   $w_{N_i}$ is a modulation wavelength assigned to the $N_i^{th}$ element value associated with an $i^{th}$ element of one of the input sequence or the reference sequence,
   S is a wavelength coding resolution,
   $k_{m,n}$ is a constant associated with an $m^{th}$ element value and an $n^{th}$ element value of the plurality of element values, and
   R is a number of successive repetitions of the $i^{th}$ element in one of the input sequence or the reference sequence.

6. The method of claim 1, wherein generating the aligned sequence comprises:
   generating a plurality of vertically repeated reference sequences from the optically coded reference sequence, each of the plurality of vertically repeated reference sequences comprising a repetition of the optically coded reference sequence shifted in a vertical direction by a first vertical shift;
   generating a plurality of horizontally repeated reference sequences from the plurality of vertically repeated reference sequences, each of the plurality of horizontally repeated reference sequences comprising a repetition of one of the plurality of vertically repeated reference sequences shifted in a horizontal direction by a first horizontal shift;
   generating a first two-dimensional image by overlapping the optically coded input sequence with each of the optically coded reference sequence, the plurality of vertically repeated reference sequences, and the plurality of horizontally repeated reference sequences, the first two-dimensional image comprising a first plurality of columns, each of the first plurality of columns comprising a first vertical arrangement of pixels, each pixel of the first vertical arrangement of pixels comprising one of a dark pixel or a bright pixel;
   generating a first optically thresholded two-dimensional image from the first two-dimensional image by replacing the bright pixel with the dark pixel in the first vertical arrangement of pixels responsive to detecting that a brightness level of the bright pixel is lower than a brightness threshold;
   generating a first one-dimensional image from the first optically thresholded two-dimensional image by projecting a first column of the first plurality of columns into a first pixel of a first pixel array, projecting the first column into the first pixel comprising including the bright pixel in the first pixel responsive to determining that the first column comprises the bright pixel; and
   extracting a first sequence of pixels from the first one-dimensional image by mapping the first pixel to a first neighboring pixels subset of the first pixel array responsive to including the bright pixel in the first pixel.

7. The method of claim 6, wherein determining the mutation in the input sequence comprises detecting a respective pair of successive dark pixels in the first sequence of pixels, the respective pair of successive dark pixels associated with the low-value element.

8. The method of claim 6, wherein generating the aligned sequence further comprises:
- generating a plurality of vertically repeated input sequences from the optically coded input sequence, each of the plurality of vertically repeated input sequences comprising a repetition of the optically coded input sequence shifted in the vertical direction by a second vertical shift;
- generating a plurality of horizontally repeated input sequences from the plurality of vertically repeated reference sequences, each of the plurality of horizontally repeated input sequences comprising a repetition of one of the plurality of vertically repeated reference sequences shifted in the horizontal direction by a second horizontal shift;
- generating a second two-dimensional image by overlapping the optically coded reference sequence with each of the optically coded input sequence, the plurality of vertically repeated input sequences, and the plurality of horizontally repeated input sequences, the second two-dimensional image comprising a second plurality of columns, each of the second plurality of columns comprising a second vertical arrangement of pixels, each pixel of the second vertical arrangement of pixels comprising one of the dark pixel or the bright pixel;
- generating a second optically thresholded two-dimensional image from the second two-dimensional image by replacing the bright pixel with the dark pixel in the second vertical arrangement of pixels responsive to detecting that the brightness level of the bright pixel is lower than the brightness threshold;
- generating a second one-dimensional image from the second optically thresholded two-dimensional image by projecting a second column of the second plurality of columns into a second pixel of a second pixel array, projecting the second column into the second pixel comprising including the bright pixel in the second pixel responsive to determining that the second column comprises the bright pixel; and
- extracting a second sequence of pixels from the second one-dimensional image by mapping the second pixel to a second neighboring pixels subset of the second pixel array responsive to including the bright pixel in the second pixel.

9. The method of claim 8, wherein determining the mutation in the input sequence comprises:
- determining a substitution in the input sequence by detecting a first pair of successive dark pixels in the first sequence of pixels and detecting a second pair of successive dark pixels in the second sequence of pixels, the first pair associated with the second pair, each of the first pair and the second pair associated with the low-value element;
- determining an insertion in the input sequence by detecting a third pair of successive dark pixels in the first sequence of pixels and detecting a fourth pair of successive bright pixels in the second sequence of pixels, the third pair associated with the fourth pair, the third pair associated with the low-value element and the fourth pair associated with the high-value element; and
- determining a deletion in the input sequence by detecting a fifth pair of successive bright pixels in the first sequence of pixels and detecting a sixth pair of successive dark pixels in the second sequence of pixels, the fifth pair associated with the sixth pair, the fifth pair associated with the high-value element and the sixth pair associated with the low-value element.

10. A system for optically detecting mutations in a sequence of DNA, the system comprising:
- a light source configured to illuminate an input optical signal;
- a first optical filter configured to generate an optically coded input signal from the input optical signal based on an input sequence, the input sequence comprising an input arrangement of a plurality of elements, each of the plurality of elements comprising an element value of a plurality of element values;
- a second optical filter configured to generate an aligned signal by overlapping the optically coded input signal with a reference sequence, the reference sequence comprising a reference arrangement of the plurality of elements; and
- a detector configured to receive and display the aligned signal.

11. The system of claim 10, wherein the first optical filter comprises:
- a first polarizer configured to generate a polarized input signal from the input optical signal; and
- a first electrically tunable color filter configured to:
  - generate a primary coded input signal from the polarized input signal by overlapping the polarized input signal with a first arrangement of a plurality of bright-pixels patterns on the first electrically tunable color filter, the first arrangement corresponding to the input arrangement, each of the plurality of bright-pixels patterns assigned to each of the plurality of elements, each of the plurality of bright-pixels patterns comprising a sequence of bright pixels, the sequence of bright pixels comprising a respective pair of successive bright pixels associated with a dual-vector (DV)-curve representation of a respective element value of the plurality of element values; and
  - generate the optically coded input signal from the primary coded input signal by modifying a wavelength of an element of the primary coded input signal based on neighboring elements of a corresponding element in the input sequence.

12. The system of claim 11, wherein the second optical filter comprises:
- a second polarizer configured to generate a polarized coded input signal from the optically coded input signal;
- a second electrically tunable color filter configured to:
  - generate a first primary image from the polarized coded input signal by overlapping the polarized coded input signal with each of a second arrangement of the plurality of bright-pixels patterns on the second electrically tunable color filter, a first plurality of vertical arrangements of the plurality of bright-pixels patterns on the second electrically tunable color filter, and a first plurality of horizontal arrangements of the plurality of bright-pixels patterns on the second electrically tunable color filter, the second arrangement corresponding to the reference arrangement, each of the first plurality of vertical arrangements comprising a repetition of the second arrangement shifted in a vertical direction of the second electrically tunable color filter by a first vertical shift, and each of the first plurality of horizontal arrangements comprising a repetition of one of the first plurality of vertical arrangements shifted in a horizontal direction of the second electrically tunable color filter by a first horizontal shift; and generate a first two-dimensional image from the first primary image by modifying a wavelength of each element of the first primary image based on neighboring elements of a corresponding element in the reference sequence, the first two-dimensional image comprising a first plurality of columns, each of the first plurality of columns comprising a first vertical arrangement of pixels, each pixel of the first vertical arrangement of pixels comprising one of a dark pixel or a bright pixel;

a first optical thresholder configured to generate a first optically thresholded two-dimensional image from the first two-dimensional image by blocking an illumination of the bright pixel responsive to detecting that a brightness level of the bright pixel is lower than a brightness threshold;

a first cylindrical lens configured to generate a first one-dimensional image from the first optically thresholded two-dimensional image by projecting a first column of the first plurality of columns into a first pixel of a first pixel array, projecting the first column into the first pixel comprising including the bright pixel in the first pixel responsive to determining that the first column comprises the bright pixel;

a first diffraction grating configured to:
  receive an illumination of the first one-dimensional image, the illumination of the first one-dimensional image comprising a first plurality of rays, each of the first plurality of rays associated with the bright pixel; and
  generate a first segment of the aligned signal by diffracting each of the plurality of rays into a first plurality of diffracted rays, the first plurality of diffracted rays associated with a first neighboring pixels subset of the first pixel array responsive to including the bright pixel in the first pixel; and a first mirror configured to reflect the first segment on the detector.

13. The system of claim 12, wherein the light source comprises:
  a laser configured to emit a beam of light;
  a beam splitter configured to split the beam into a first split beam and a second split beam;
  a second diffraction grating configured to diffract the first split beam into a first plurality of diffracted beams;
  a first optical lens configured to generate the input optical signal by producing a first plurality of parallel beams from the first plurality of diffracted beams;
  a second mirror configured to produce a reflection of the second split beam;
  a third diffraction grating configured to diffract the reflection of the second split beam into a second plurality of diffracted beams; and
  a second optical lens configured to generate a reference optical signal by producing a second plurality of parallel beams from the second plurality of diffracted beams.

14. The system of claim 13, further comprising:
a third optical filter, comprising:
  a third polarizer configured to generate a polarized reference signal from the reference optical signal; and
  a third electrically tunable color filter configured to:
    generate a primary coded reference signal from the polarized reference signal by overlapping the polarized reference signal with a third arrangement of the plurality of bright-pixels patterns on the third electrically tunable color filter, the third arrangement corresponding to the reference arrangement; and
    generate an optically coded reference signal from the primary coded reference signal by modifying a wavelength of each element of the primary coded reference signal based on neighboring elements of a corresponding element in the reference sequence;

a fourth optical filter, comprising:
  a fourth polarizer configured to generate a polarized coded reference signal from the optically coded reference signal based on the input arrangement;
  a fourth electrically tunable color filter configured to:
    generate a second primary image from the polarized coded reference signal by overlapping the polarized coded reference signal with each of a fourth arrangement of the plurality of bright-pixels patterns on the fourth electrically tunable color filter, a second plurality of vertical arrangements of the plurality of bright-pixels patterns on the fourth electrically tunable color filter, and a second plurality of horizontal arrangements of the plurality of bright-pixels patterns on the fourth electrically tunable color filter, the fourth arrangement corresponding to the input arrangement, each of the second plurality of vertical arrangements comprising a repetition of the fourth arrangement shifted in a vertical direction of the fourth electrically tunable color filter by a second vertical shift, and each of the second plurality of horizontal arrangements comprising a repetition of one of the second plurality of vertical arrangements shifted in a horizontal direction of the fourth electrically tunable color filter by a second horizontal shift; and
    generate a second two-dimensional image from the second primary image by modifying a wavelength of an element of the second primary image based on neighboring elements of a corresponding element in the input sequence, the second two-dimensional image comprising a second plurality of columns, each of the second plurality of columns comprising a second vertical arrangement of pixels, each pixel of the second vertical arrangement of pixels comprising one of the dark pixel or the bright pixel;

a second optical thresholder configured to generate a second optically thresholded two-dimensional image from the second two-dimensional image by blocking an illumination of the bright pixel responsive to detecting that a brightness level of the bright pixel is lower than a brightness threshold;

a second cylindrical lens configured to generate a second one-dimensional image from the second optically thresholded two-dimensional image by projecting a second column of the second plurality of columns into a second pixel of a second pixel array, projecting the second column into the second pixel comprising including the bright pixel in the second pixel responsive to determining that the second column comprises the bright pixel;

a fourth diffraction grating configured to:
  receive an illumination of the second one-dimensional image, the illumination of the second one-dimensional image comprising a second plurality of rays, each of the second plurality of rays associated with the bright pixel; and generate the second segment of the aligned signal by diffracting each of the second plurality of rays into a second plurality of diffracted rays, the second plurality of diffracted rays associated with a second neighboring pixels subset of the second pixel array responsive to including the bright pixel in the second pixel; and a third mirror configured to reflect the second segment on the detector.

15. The system of claim 14, wherein each of the modified wavelength of the element of the primary coded input signal and the modified wavelength of the element of the second primary image comprises a wavelength $W_{N_i}$ of an $N_i^{th}$ element value of the plurality of element values, the wavelength $W_{N_i}$ given by the following:

$$W_{N_i} = w_{N_i} - (4 \times S \times k_{N_i,N_i-1}) - S \times k_{N_i,N_i+1} + S(R-1),$$

where:

$w_{N_i}$ is a modulation wavelength of the $N_i^{th}$ element value associated with an $i^{th}$ element of one of the input sequence or the reference sequence, S is a wavelength coding resolution, $k_{m,n}$ is a constant associated with an $m^{th}$ element value and an $n^{th}$ element value of the plurality of element values, and R is a number of successive repetitions of the $i^{th}$ element in one of the input sequence or the reference sequence.

16. The system of claim 14, wherein each of the first electrically tunable color filter, the second electrically tunable color filter, the third electrically tunable color filter, and the fourth electrically tunable color filter comprises a plurality of graphene-based spatial light modulators, a graphene-based spatial light modulator of the plurality of graphene-based spatial light modulators configured to prevent transmission of a light beam associated with a wavelength range responsive to a voltage applied to the graphene-based spatial light modulator, the graphene-based spatial light modulator comprising:

a conductive layer;

a dielectric layer mounted on the conductive layer; and a graphene layer mounted on the dielectric layer, the graphene layer comprising a plurality of parallel graphene sheets.

17. The system of claim 16, wherein the conductive layer comprises a gold nanostructure.

18. The system of claim 16, wherein the dielectric layer comprises a silicon dioxide material.

19. The system of claim 16, wherein a space between each adjacent graphene sheets of the plurality of parallel graphene sheets lies in a range of 95 nm and 105 nm.

20. The system of claim 16, wherein a width of each of the plurality of parallel graphene sheets lies in a range of 195 nm and 205 nm.

* * * * *